(12) United States Patent
Ishikawa

(10) Patent No.: US 10,843,040 B2
(45) Date of Patent: Nov. 24, 2020

(54) EXERCISE ANALYSIS DEVICE, EXERCISE ANALYSIS METHOD, PROGRAM, RECORDING MEDIUM, AND EXERCISE ANALYSIS SYSTEM

(71) Applicant: SEIKO EPSON CORPORATION, Tokyo (JP)

(72) Inventor: Masaki Ishikawa, Kunitachi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 80 days.

(21) Appl. No.: 15/540,236

(22) PCT Filed: Dec. 10, 2015

(86) PCT No.: PCT/JP2015/006168
§ 371 (c)(1),
(2) Date: Jun. 27, 2017

(87) PCT Pub. No.: WO2016/113796
PCT Pub. Date: Jul. 21, 2016

(65) Prior Publication Data
US 2017/0348560 A1 Dec. 7, 2017

(30) Foreign Application Priority Data
Jan. 13, 2015 (JP) .................. 2015-004347

(51) Int. Cl.
*A63F 9/24* (2006.01)
*A63B 24/00* (2006.01)
(Continued)

(52) U.S. Cl.
CPC ........ *A63B 24/0003* (2013.01); *A61B 5/1121* (2013.01); *A61B 5/6895* (2013.01);
(Continued)

(58) Field of Classification Search
CPC .................................................. A63B 69/3617
(Continued)

(56) References Cited

U.S. PATENT DOCUMENTS 4,165,071 A 8/1979 Frolow
4,291,574 A 9/1981 Frolow
(Continued)

FOREIGN PATENT DOCUMENTS

JP H03-126477 A 5/1991
JP H04-141186 A 5/1992
(Continued)

OTHER PUBLICATIONS

Mar. 8, 2016 International Search Report issued in International Patent Application No. PCT/JP2015/006168.

*Primary Examiner* — Raeann Gorden
(74) *Attorney, Agent, or Firm* — Oliff PLC

(57) ABSTRACT

The sensor information acquisition unit acquires an angular velocity around an axis of a shaft portion of an exercise instrument from a sensor unit. An exercise analysis unit detects a timing of an impact of the exercise instrument. A calculation unit calculates a distance between a standard position set on a hitting surface of the exercise instrument and a position of the hitting based on the angular velocity at the time of an impact.

11 Claims, 23 Drawing Sheets

EXERCISE ANALYSIS SYSTEM 1

(51) Int. Cl.
  *A61B 5/11* (2006.01)
  *A61B 5/00* (2006.01)
  *A63B 69/36* (2006.01)
  *A63B 69/00* (2006.01)
  *A63B 69/38* (2006.01)
  *A63B 71/06* (2006.01)

(52) U.S. Cl.
  CPC ........ *A61B 5/7246* (2013.01); *A63B 69/0002* (2013.01); *A63B 69/36* (2013.01); *A63B 69/38* (2013.01); *A63B 71/0622* (2013.01); *A61B 5/1122* (2013.01); *A61B 5/1128* (2013.01); *A61B 5/7282* (2013.01); *A61B 2562/0219* (2013.01); *A63B 2069/0008* (2013.01); *A63B 2220/40* (2013.01); *A63B 2220/62* (2013.01); *A63B 2220/803* (2013.01); *A63B 2220/833* (2013.01); *A63B 2225/50* (2013.01)

(58) Field of Classification Search
  USPC ....................................................... 473/223
  See application file for complete search history.

(56) References Cited

U.S. PATENT DOCUMENTS

| | | |
|---|---|---|
| 5,233,544 A | 8/1993 | Kobayashi |
| 5,332,225 A | 7/1994 | Ura |
| 10,456,621 B2 * | 10/2019 | Onuki ................ A63B 24/0003 |
| 2011/0086720 A1 | 4/2011 | Jaekel et al. |
| 2011/0183780 A1 | 7/2011 | Leech et al. |
| 2012/0157241 A1 | 6/2012 | Nomura et al. |
| 2016/0001128 A1 | 1/2016 | Nomura et al. |

FOREIGN PATENT DOCUMENTS

| | | |
|---|---|---|
| JP | H06-000237 A | 1/1994 |
| JP | 2002-017932 A | 1/2002 |
| JP | 2009-005715 A | 1/2009 |
| JP | 2009-125499 A | 6/2009 |
| JP | 2010-284177 A | 12/2010 |
| JP | 2011-156357 A | 8/2011 |
| JP | 2012-130414 A | 7/2012 |
| JP | 2012-130415 A | 7/2012 |
| JP | 2013-188239 A | 9/2013 |

* cited by examiner

| GyroY (rad/s) | HS(m/s) | GyroY/HS | HITTING POINT MEASUREMENT VALUE (mm) |
|---|---|---|---|
| −114.6 | 1.7 | −68.8 | 8 |
| 186.9 | 1.6 | 114.6 | −7 |
| 194.1 | 1.5 | 127.0 | −8 |
| −259.6 | 1.5 | −177.4 | 18 |
| −263.4 | 2.3 | −115.3 | 12 |
| 186.0 | 1.9 | 95.8 | −7 |
| −197.4 | 2.2 | −90.0 | 10 |
| 126.7 | 1.8 | 68.7 | −5 |
| 83.5 | 1.7 | 48.5 | −2 |
| −106.0 | 1.0 | −101.4 | 13 |
| 202.3 | 1.0 | 211.6 | −16 |
| −248.8 | 1.1 | −229.5 | 25 |
| −97.2 | 1.0 | −98.0 | 10 |

FIG. 11

| GyroY (rad/s) | HS(m/s) | GyroY/HS | HITTING POINT MEASUREMENT VALUE (mm) |
|---|---|---|---|
| -67.0 | 1.2 | -53.6 | 9 |
| -50.9 | 1.2 | -42.1 | 6 |
| -84.2 | 1.3 | -65.6 | 10 |
| 37.0 | 1.1 | 33.2 | -4 |
| 8.5 | 1.4 | 5.9 | 0 |
| 51.8 | 1.2 | 42.5 | -8 |
| -183.0 | 1.3 | -138.6 | 22 |
| -51.3 | 1.4 | -35.7 | 4 |
| -72.7 | 1.5 | -49.4 | 9 |
| 68.9 | 1.4 | 48.1 | 8 |

| GyroY (rad/s) | HS (m/s) | GyroY/HS | HORIZONTAL HITTING POINT MEASUREMENT VALUE (mm) | HEIGHT HITTING POINT MEASUREMENT VALUE (mm) | HEIGHT CORRECTION HORIZONTAL HITTING POINT POSITION (mm) |
|---|---|---|---|---|---|
| −225.7 | 1.9 | −117.4 | 6 | 12 | 7.5 |
| −125.0 | 1.7 | −72.9 | 3 | 9 | 3.4 |
| 56.7 | 2.0 | 28.7 | −1 | 5 | −2.1 |
| −342.7 | 1.9 | −184.0 | 15 | 6 | 14.3 |
| −74.0 | 1.6 | −45.5 | −1 | 9 | −0.6 |
| −304.4 | 1.9 | −159.0 | 13 | 7 | 12.6 |
| −376.3 | 2.1 | −178.8 | 14 | 7 | 13.6 |
| 205.1 | 1.9 | 108.9 | −9 | 8 | −9.0 |
| 124.8 | 1.9 | 66.1 | −3 | 4 | −4.5 |

$y = -0.0771x - 0.8344$
$R^2 = 0.9675$

| GyroY (rad/s) | HS (m/s) | GyroY/HS | HORIZONTAL HITTING POINT MEASUREMENT VALUE (mm) | HEIGHT HITTING POINT MEASUREMENT VALUE (mm) | HEIGHT CORRECTION HORIZONTAL HITTING POINT POSITION (mm) |
|---|---|---|---|---|---|
| −225.7 | 1.9 | −117.4 | 6 | 12 | 13.0 |
| −125.0 | 1.7 | −72.9 | 3 | 9 | 7.5 |
| 56.7 | 2.0 | 28.7 | −1 | 5 | 0.2 |
| −342.7 | 1.9 | −184.0 | 15 | 6 | 17.0 |
| −74.0 | 1.6 | −45.5 | −1 | 9 | 3.5 |
| −304.4 | 1.9 | −159.0 | 13 | 7 | 15.8 |
| −376.3 | 2.1 | −178.8 | 14 | 7 | 16.8 |
| 205.1 | 1.9 | 108.9 | −9 | 8 | −5.3 |
| 124.8 | 1.9 | 66.1 | −3 | 4 | −2.7 | y = −0.0797x + 2.4095
R² = 0.9837

EXERCISE ANALYSIS DEVICE, EXERCISE ANALYSIS METHOD, PROGRAM, RECORDING MEDIUM, AND EXERCISE ANALYSIS SYSTEM

TECHNICAL FIELD

The present invention relates to an exercise analysis device, an exercise analysis method, a program, a recording medium, and an exercise analysis system.

BACKGROUND ART

PTL 1 discloses that rotation around a shaft axis of an exercise instrument is measured and it is determined whether hitting is within a sweet spot based on a rotation amount. In PTL 1, a user can ascertain whether hitting is within a sweet spot.

CITATION LIST

Patent Literature

PTL 1: JP-A-2012-130415

SUMMARY OF INVENTION

Technical Problem

However, it is not disclosed that a user specifically indicates how much hitting deviates from a sweet spot.

Accordingly, an object of the invention is to provide a technology for enabling to ascertain how much hitting deviates from a standard position set on a hitting surface of an exercise instrument.

Solution to Problem

A first aspect of the invention to solve the foregoing problem is directed to an exercise analysis device including: an acquisition unit that acquires an angular velocity generated around an axis in a longitudinal direction of a shaft portion of an exercise instrument; a detection unit that detects an impact of hitting in a swing; and a calculation unit that calculates a distance between a standard position set on a hitting surface of a hitting portion of the exercise instrument and a position of the hitting based on the angular velocity generated due to the impact.

According to the first aspect, a user can ascertain a deviation in the position of the hitting from the standard position set on the hitting surface of the exercise instrument.

The calculation unit may calculate the distance with reference to relation information acquired in advance and indicating correlation between the angular velocity and the distance.

With this configuration, the calculation unit can calculate the distance of the position of the hitting using the relation information.

An angular velocity based on the relation information may be acquired in advance and may be divided by a speed of the hitting portion at the time of an impact. The calculation unit may divide the angular velocity generated by an impact of the hitting portion of the swung exercise instrument by the speed of the hitting portion at the time of the impact and calculate the distance with reference to the relation information based on a value obtained through the division.

With this configuration, the exercise analysis device can calculate a distance of a more accurate position of the hitting.

The relation information may be acquired according to a shape of the hitting portion in advance. The calculation unit may calculate the distance according to the shape of the hitting portion of the swung exercise instrument with reference to the relation information.

With this configuration, the exercise analysis device can calculate a distance of a more accurate position of the hitting according to the shape of the exercise instrument.

An angular velocity based on the relation information may be divided by a takeback distance acquired in advance. The calculation unit may divide the angular velocity generated by an impact of the hitting portion of the swung exercise instrument by the takeback distance of the swung exercise instrument and calculate the distance with reference to the relation information based on a value obtained through the division.

With this configuration, the exercise analysis device can calculate a distance of a more accurate position of the hitting.

An angular velocity based on the relation information may be divided by a takeback angle acquired in advance. The calculation unit may divide the angular velocity generated by an impact of the hitting portion of the swung exercise instrument by the takeback angle of the swung exercise instrument and calculate the distance with reference to the relation information based on a value obtained through the division.

With this configuration, the exercise analysis device can calculate a distance of a more accurate position of the hitting.

The calculation unit may calculate an average value of the angular velocities before an impact of the hitting portion of the swung exercise instrument and calculate the distance based on a value obtained by subtracting the average value from the angular velocity generated by the impact.

With this configuration, the exercise analysis device can calculate a distance of a more accurate position of the hitting.

A second aspect of the invention to solve the foregoing problem is directed to an exercise analysis method including the steps of: acquiring an angular velocity generated around an axis in a longitudinal direction of a shaft portion of an exercise instrument; detecting an impact of hitting in a swing; and calculating a distance between a standard position set on a hitting surface of a hitting portion of the exercise instrument and a position of the hitting based on the angular velocity generated due to the impact.

According to the second aspect, a user can ascertain a deviation in the position of the hitting from the standard position set on the hitting surface of the exercise instrument.

In the calculating step, the distance may be calculated with reference to relation information acquired in advance and indicating correlation between the angular velocity and the distance.

With this configuration, the calculation unit can calculate the distance of the position of the hitting using the relation information.

An angular velocity based on the relation information may be acquired in advance and may be divided by a speed of the hitting portion at the time of an impact. The calculating step may include dividing the angular velocity generated by an impact of the hitting portion of the swung exercise instrument by the speed of the hitting portion at the time of the impact and calculating the distance with reference to the relation information based on a value obtained through the division.

With this configuration, the exercise analysis device can calculate a distance of a more accurate position of the hitting.

The relation information may be acquired according to a shape of the hitting portion in advance. The calculating step may include calculating the distance according to the shape of the hitting portion of the swung exercise instrument with reference to the relation information.

With this configuration, the exercise analysis device can calculate a distance of a more accurate position of the hitting according to the shape of the exercise instrument.

An angular velocity based on the relation information may be divided by a takeback distance acquired in advance. The calculating step may include dividing the angular velocity generated by an impact of the hitting portion of the swung exercise instrument by the takeback distance of the swung exercise instrument and calculating the distance with reference to the relation information based on a value obtained through the division.

With this configuration, the exercise analysis device can calculate a distance of a more accurate position of the hitting.

A third aspect of the invention to solve the foregoing problem is directed to a program causing a computer to perform the steps of: acquiring an angular velocity generated around an axis in a longitudinal direction of a shaft portion of an exercise instrument; detecting an impact of hitting in a swing; and calculating a distance between a standard position set on a hitting surface of a hitting portion of the exercise instrument and a position of the hitting based on the angular velocity generated due to the impact.

According to the third aspect, a user can ascertain a deviation in the position of the hitting from the standard position set on the hitting surface of the exercise instrument.

Another aspect of the invention to solve the foregoing problem is directed to a recording medium that records a program causing a computer to perform the steps of: acquiring an angular velocity generated around an axis in a longitudinal direction of a shaft portion of an exercise instrument; detecting an impact of hitting in a swing; and calculating a distance between a standard position set on a hitting surface of a hitting portion of the exercise instrument and a position of the hitting based on the angular velocity generated due to the impact.

According to the another aspect, a user can ascertain a deviation in the position of the hitting from the standard position set on the hitting surface of the exercise instrument.

A fourth aspect of the invention to solve the foregoing problem is directed to an exercise analysis system that includes: an inertial sensor that measures an angular velocity generated around an axis in a longitudinal direction of a shaft portion of an exercise instrument; and an exercise analysis device including an acquisition unit that acquires the angular velocity, a detection unit that detects an impact of hitting in a swing, and a calculation unit that calculates a distance between a standard position set on a hitting surface of a hitting portion of the exercise instrument and a position of the hitting based on the angular velocity generated due to the impact.

According to the fourth aspect, a user can ascertain a deviation in the position of the hitting from the standard position set on the hitting surface of the exercise instrument.

BRIEF DESCRIPTION OF DRAWINGS

FIG. 11 is a diagram illustrating an example of relation information according to a second embodiment.

DESCRIPTION OF EMBODIMENTS

Hereinafter, embodiments of the invention will be described with reference to the drawings. Hereinafter, an exercise analysis system that analyzes a golf swing will be described as an example.

First Embodiment

Figure 1:
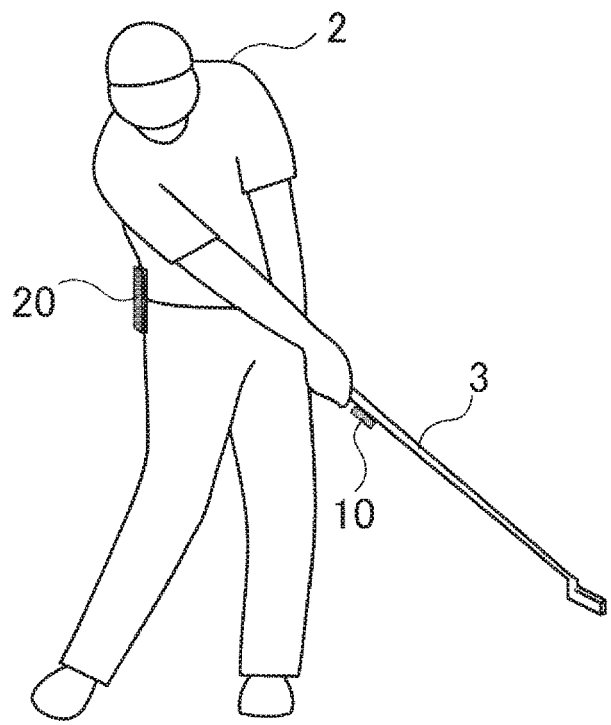
FIG. 1 is a diagram illustrating an overview of an exercise analysis system according to a first embodiment of the invention.

FIG. 1 is a diagram illustrating an overview of an exercise analysis system according to a first embodiment of the invention.

An exercise analysis system 1 includes a sensor unit 10 and an exercise analysis device 20.

The sensor unit 10 is an inertial sensor, can measure acceleration generated in each an axial direction of three axes and an angular velocity generated around each axis of the three axes, and is worn on a golf club 3. The sensor unit 10 is worn on a part of a shaft portion of the golf club 3 by matching one axis of three detection axes (the x, y, and z axes), for example, the y axis, to the major axis direction of the shaft portion. Preferably, the sensor unit 10 is worn at a position close to a grip portion to which an impact at the time of a shot is rarely transmitted and a centrifugal force is not applied at the time of a swing. The shaft portion is a handle portion excluding the head of the golf club 3 and includes the grip portion.

A user 2 performs a swing motion to hit a golf ball (not illustrated) according to a pre-decided procedure. For example, the user 2 first grasps the golf club 3, takes an address attitude so that the major axis of the shaft portion of the golf club 3 is perpendicular to a target line (for example, a target direction of hitting), and is at a standstill for a predetermined time or more (for example, 1 or more seconds). Next, the user 2 performs the swing motion to hit and fly the golf ball. In the present specification, the address attitude includes an attitude of a standstill state of the user before start of the swing or an attitude of a state in which the user oscillates (waggles) the exercise instrument before starting the swing.

While the user 2 performs the motion to hit the golf ball according to the above-described procedure, the sensor unit measures triaxial acceleration and triaxial angular velocities at a predetermined period (for example, 1 ms) and sequentially transmits measured data to the exercise analysis device 20. The sensor unit 10 may immediately transmit the measured data or may store the measured data in an internal memory and transmit the measured data at a desired timing such as an end of a swing motion of the user 2. Communication between the sensor unit 10 and the exercise analysis device 20 may be wireless communication or may be wired communication.

Alternatively, the sensor unit 10 may store the measured data in a detachable recording medium such as a memory card and the exercise analysis device 20 may read the measured data from the recording medium.

The exercise analysis device 20 analyzes a hitting position of the ball on the head of the golf club 3 in the horizontal direction (right and left directions) using the data measured by the sensor unit 10. The exercise analysis device 20 generates image data including information regarding the analyzed hitting position and causes the display unit to display an image according to the image data.

The exercise analysis device 20 is, for example, a portable device such as a smartphone or a personal computer (PC). In FIG. 1, the exercise analysis device 20 is worn on the waist of the user 2, but the worn position is not particularly limited. The exercise analysis device 20 may not be worn by the user 2.

Figure 2:
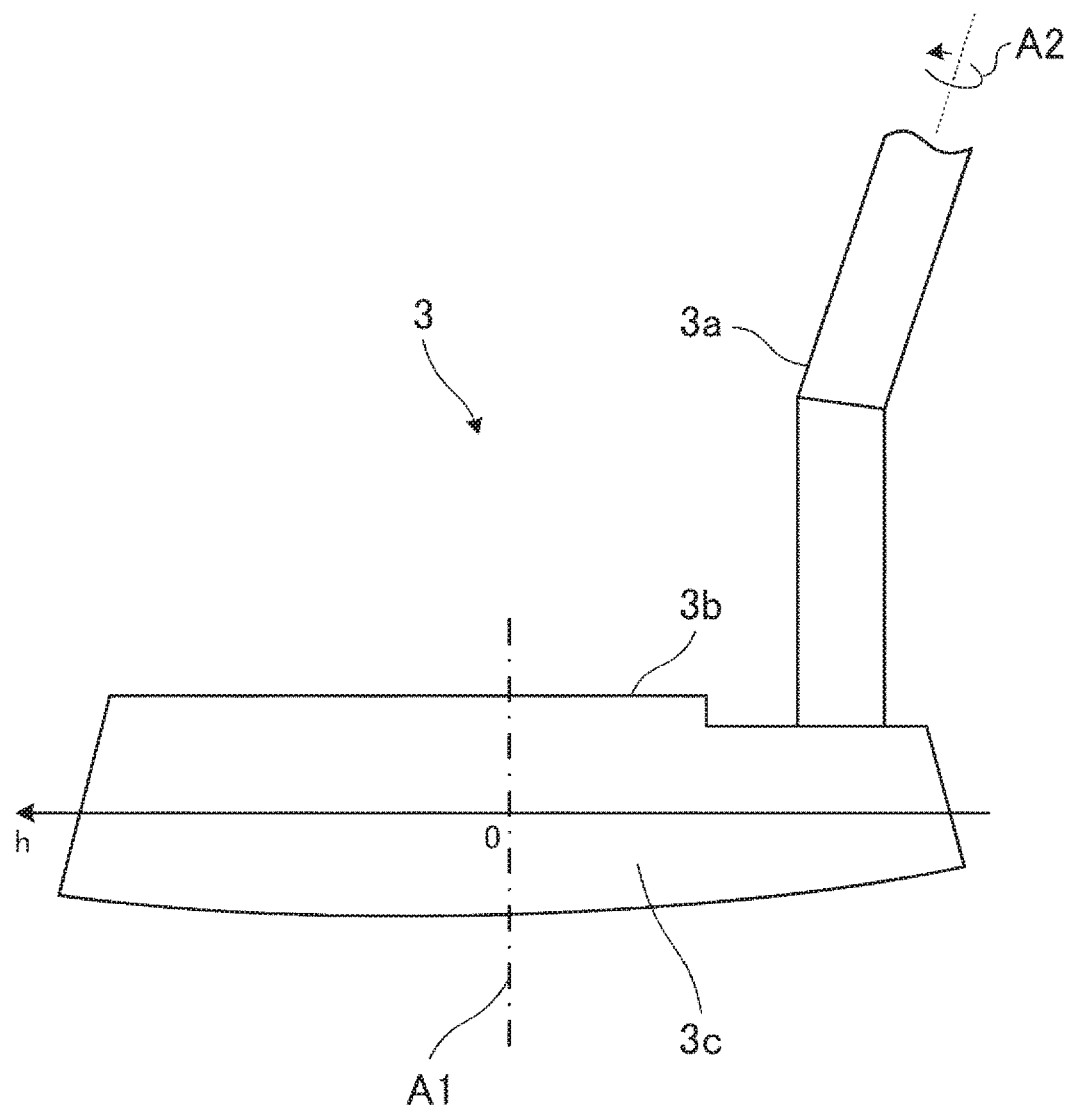
FIG. 2 is a diagram for describing a hitting position of a head of a golf club.

FIG. 2 is a diagram for describing a hitting position of a head of a golf club. In FIG. 2, a part of a shaft portion 3a and a hitting portion (head) 3b of the golf club 3 are illustrated. The hitting portion 3b has a hitting surface 3c on which a ball is hit. The golf club 3 is, for example, a putter.

A one-dot chain line A1 illustrated in FIG. 2 indicates a sweet spot of the hitting surface 3c of the golf club 3 in the horizontal direction. In general, when the user 2 can capture the ball at the sweet spot indicated by the one-dot chain line A1, the user 2 can roll the ball straight and smoothly.

In FIG. 2, an h axis parallel to the horizontal direction is illustrated. In FIG. 2, a point at which the h axis intersects the sweet spot is set as the origin (O) of the h axis. In FIG. 2, a sheet right direction (the direction of the shaft portion 3a) from the origin of the h axis is set to be negative and a sheet left direction (an opposite direction to the shaft portion 3a) from the origin of the h axis is set to be positive.

An arrow A2 in FIG. 2 indicates rotation around a major axis of the shaft portion 3a. It is recognized that an angular velocity around the major axis of the shaft portion 3a at the time of an impact has correlation with deviation in a hitting position of a ball from the sweet spot.

For example, an angular velocity around the major axis of the shaft portion 3a at the time of an impact generally increases as the absolute value of a hitting position "h" of a ball increases. For example, as the hitting position of a ball is more distant from the one-dot chain line A1 in the horizontal direction, an angular velocity around the major axis of the shaft portion 3a generally increases.

A rotation direction around the major axis of the shaft portion 3a at the time of an impact is generally reversed in accordance with a positive or negative sign of the hitting position "h" of a ball. For example, in a case in which a value of the hitting position "h" of a ball is positive, a rotation direction around the major axis of the shaft portion 3a is generally an opposite direction (a direction in which the hitting surface 3c is open) to a direction indicated by the arrow A2.

In this way, it is recognized that an angular velocity around the major axis of the shaft portion 3a has correlation with a deviation in a hitting position of a ball from a sweet spot. That is, the exercise analysis device 20 can calculate a hitting position of a ball in the horizontal direction of the hitting surface 3c (the h axis direction) using an angular velocity around the major axis of the shaft portion 3a at the time of an impact. Hereinafter, for an angular velocity around the major axis of the shaft portion 3a, the direction of the arrow A2 (a direction in which the hitting surface 3c is open) is assumed to be "positive".

Figure 3:
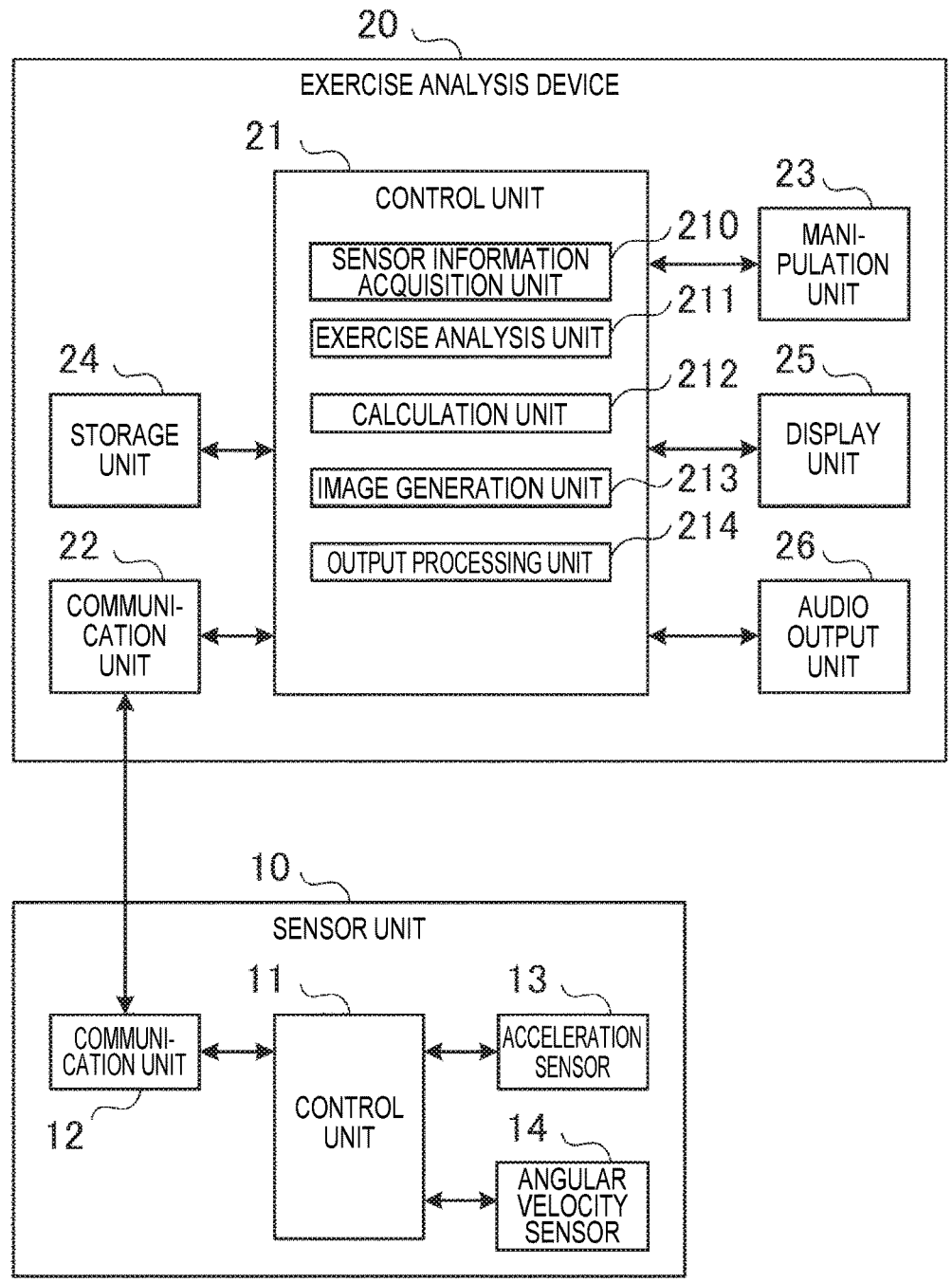
FIG. 3 is a block diagram illustrating an example of the configuration of an exercise analysis system.

FIG. 3 is a block diagram illustrating an example of the configuration of an exercise analysis system. The sensor unit 10 includes a control unit 11, a communication unit 12, an acceleration sensor 13, and an angular velocity sensor 14.

The acceleration sensor 13 measures acceleration generated in each of triaxial directions that intersect each other (ideally, are perpendicular to each other) and outputs digital signals (acceleration data) according to the magnitudes and directions of the measured triaxial acceleration.

The angular velocity sensor 14 measures an angular velocity generated around each axis of three axes that intersect each other (ideally, are perpendicular to each other)

and outputs digital signals (angular velocity data) according to the magnitudes and directions of the measured triaxial angular velocities.

The control unit 11 integrally controls the sensor unit. The control unit 11 receives the acceleration data and the angular velocity data from the acceleration sensor 13 and the angular velocity sensor 14, respectively, adds time information, and stores the acceleration data and the angular velocity data in a storage unit (not illustrated). The control unit 11 adds time information to the stored measured data (the acceleration data and the angular velocity data), generates packet data adapted to a communication format, and outputs the packet data to the communication unit 12.

Ideally, the acceleration sensor 13 and the angular velocity sensor 14 are each mounted on the sensor unit 10 so that the three axes match three axes (x, y, and z axes) of a rectangular coordinate system (sensor coordinate system) defined in the sensor unit 10. However, actually, there is a mounting angle error. Accordingly, the control unit 11 performs a process of converting the acceleration data and the angular velocity data into data of an xyz coordinate system using correction parameters calculated in advance according to the mounting angle error.

Further, the control unit 11 may perform a temperature correction process of the acceleration sensor 13 and the angular velocity sensor 14. Alternatively, a temperature correction function may be embedded in the acceleration sensor 13 and the angular velocity sensor 14.

The acceleration sensor 13 and the angular velocity sensor 14 may output analog signals. In this case, the control unit 11 may generate measured data (acceleration data and angular velocity data) by performing analog/digital (A/D) conversion on an output signal of the acceleration sensor 13 and an output signal of the angular velocity sensor 14 and may generate communication packet data using the measured data.

The communication unit 12 performs a process of transmitting the packet data received from the control unit 11 to the exercise analysis device 20 or a process of receiving a control command from the exercise analysis device 20 and sending the control command to the control unit 11. The control unit 11 performs various processes according to the control command.

The exercise analysis device 20 includes a control unit 21, a communication unit 22, a manipulation unit 23, a storage unit 24, a display unit 25, and an audio output unit 26.

The communication unit 22 receives the packet data transmitted from the sensor unit 10 and performs a process of sending the packet data to the control unit 21 or a process of transmitting the control command from the control unit 21 to the sensor unit 10.

The manipulation unit 23 performs a process of acquiring manipulation data from the user and sending the manipulation data to the control unit 21. The manipulation unit 23 may be, for example, a touch panel display, a button, a key, or a microphone.

The storage unit 24 is configured to include, for example, various IC memories such as a read-only memory (ROM), a flash ROM, and a random access memory (RAM) or a recording medium such as a hard disk or a memory card.

The storage unit 24 stores a program used for the control unit 21 to perform various calculation processes or control processes or various programs and data for realizing application functions. In particular, in the embodiment, the storage unit 24 stores an exercise analysis program which is read by the control unit 21 to perform an exercise analysis process. The exercise analysis program may be stored in advance in a nonvolatile recording medium, and the control unit 21 may receive the exercise analysis program from a server via a network and store the exercise analysis program in the storage unit 24.

In the embodiment, the storage unit 24 stores body information regarding the user 2, club specification information indicating the specification of the golf club 3, and sensor-mounted position information. For example, the user 2 manipulates the manipulation unit 23 and inputs body information such as a height, a weight, and a sex, the input body information is stored as body information in the storage unit 24. For example, the user 2 manipulates the manipulation unit 23, inputs a model number of the golf club 3 to be used (alternatively selects a model number from a model number list), and sets specification information of the input model number among pieces of specification information (for example, information regarding the length, a central position, a lie angle, a face angle, and a loft angle of the shaft) of model numbers stored in advance in the storage unit 24 as club specification information. For example, the user 2 manipulates the manipulation unit 23 and inputs a distance between the position at which the sensor unit 10 is mounted and the grip end of the golf club 3. Then, information regarding the input distance is stored as sensor-mounted position information in the storage unit 24. Alternatively, by mounting the sensor unit 10 at a decided predetermined position (for example, a distance of 20 cm from the grip end), information regarding the predetermined position may be stored as sensor-mounted position information in advance.

The storage unit 24 is used as a work area of the control unit 21 and temporarily stores data input from the manipulation unit 23, calculation results executed according to various programs by the control unit 21, and the like. Further, the storage unit 24 may store data necessary to be stored for a long time among pieces of data generated through processes by the control unit 21.

The display unit 25 displays a processing result of the control unit 21 as a letter, a graph, a table, an animation, or another image. The display unit 25 may be, for example, a display in which a cathode-ray tube (CRT) display, a liquid crystal display (LCD), an electrophorectic display (EPD), or an organic light-emitting diode (OLED) is used, a touch panel display, or a head-mounted display (HMD). Functions of the manipulation unit 23 and the display unit 25 may be realized by one touch panel display.

The audio output unit 26 outputs a processing result of the control unit 21 as audio such as voice or a buzzer sound. The audio output unit 26 may be, for example, a speaker or a buzzer.

The control unit 21 performs a process of transmitting a control command to the sensor unit 10, various calculation processes on data received from the sensor unit 10 via the communication unit 22, or other various control processes according to various programs. In particular, in the embodiment, the control unit 21 functions as a sensor information acquisition unit 210 (equivalent to an acquisition unit according to the invention), an exercise analysis unit 211 (equivalent to a detection unit according to the invention), a calculation unit 212, an image generation unit 213, and an output processing unit 214 by executing the exercise analysis program.

The control unit 21 may be realized by, for example, a computer that includes a central processing unit (CPU) which is an arithmetic device, a random access memory (RAM) which is a volatile storage device, a ROM which is a nonvolatile storage device, an interface (I/F) circuit which connects the control unit 21 to other units, and a bus which connects these units to each other. The computer may include various dedicated processing circuits such as an image processing circuit. The control unit 21 may be realized by an application specific integrated circuit (ASIC) or the like.

The sensor information acquisition unit 210 receives the packet data received from the sensor unit 10 by the communication unit 22 and acquires the time information and the measured data from the received packet data. The acquired measured data include an angular velocity around the major axis of the shaft portion 3a of the golf club 3 generated in swing of the user 2. The sensor information acquisition unit 210 stores the acquired time information and measured data in the storage unit 24 in association therewith.

The exercise analysis unit 211 performs a process of analyzing a swing motion of the user 2 using the measured data output by the sensor unit 10. Specifically, first, the exercise analysis unit 211 calculates an offset amount included in the measured data using the measured data (the acceleration data and the angular velocity data) at the time of a standstill (the time of an address) of the user 2 stored in the storage unit 24. Next, the exercise analysis unit 211 performs bias correction by subtracting an offset amount from the measured data after swing start stored in the storage unit 24 and calculates a position and an attitude of the sensor unit 10 during a swing motion of the user 2 using the measured data subjected to the bias correction.

For example, the exercise analysis unit 211 calculates a position (initial position) of the sensor unit 10 at the time of a standstill of the user 2 in an XYZ coordinate system (which is, for example, a coordinate system in which a position of the hitting portion 3b at the time of a standstill (the time of an address) of the user 2 is the origin, a target direction of hitting is the X axis, a axis perpendicular to the X axis on a horizontal plane is the Y axis, and an upward vertical direction is the Z axis and is referred to as a global coordinate system below) using the acceleration data measured by the acceleration sensor 13, the club specification information, and the sensor-mounted position information, and then chronologically calculates a change in the position of the sensor unit 10 from the initial position by integrating the subsequent acceleration data. Since the user 2 is at standstill at a predetermined address attitude, the X coordinate of the initial position of the sensor unit 10 is 0. Further, the y axis of the sensor unit 10 matches the major axis direction of the shaft of the golf club 3 and the acceleration sensor 13 measures only gravitational acceleration at the time of a standstill of the user 2. Therefore, the exercise analysis unit 211 can calculate an inclination angle (an inclination with respect to the horizontal plane (XY plane) or the vertical plane (XZ plane)) of the shaft using y axis acceleration data. Then, the exercise analysis unit 211 can calculate the Y and Z coordinates of the initial position of the sensor unit 10 using the inclination angle of the shaft, the club specification information (the length of the shaft), and the sensor-mounted position information (a distance from the grip end) and can specify the initial position of the sensor unit 10. Alternatively, the exercise analysis unit 211 may calculate the coordinates of the initial position of the sensor unit 10 using the coordinates of the position of the grip end of the golf club 3 and the sensor-mounted position information (the distance from the grip end).

The exercise analysis unit 211 calculates an attitude (initial attitude) of the sensor unit 10 at the time of a standstill (the time of an address) of the user 2 in the XYZ coordinate system (global coordinate system) using the acceleration data measured by the acceleration sensor 13 and chronologically calculates a change in the attitude from the initial attitude of the sensor unit 10 by performing rotation calculation using the angular velocity data subsequently measured by the angular velocity sensor 14. The attitude of the sensor unit 10 can be expressed by rotation angles (a roll angle, a pitch angle, and a yaw angle) of the X, Y, and Z axes, an Eulerian angle, a quaternion, or the like. At the time of a standstill of the user 2, the acceleration sensor 13 can measure only gravitational acceleration. Therefore, the exercise analysis unit 211 can specify an angle between a gravity direction and each of the x, y, and z axes of the sensor unit 10 using triaxial acceleration data. Further, since the user 2 is at a standstill at a predetermined address attitude, the y axis of the sensor unit 10 is on the YZ plane at the time of a standstill of the user 2. Therefore, the exercise analysis unit 211 can specify the initial attitude of the sensor unit 10.

The signal processing unit of the sensor unit 10 may calculate an offset amount of the measured data and perform bias correction of the measured data or a bias correction function may be embedded in the acceleration sensor 13 and the angular velocity sensor 14. In this case, it is not necessary for the exercise analysis unit 211 to perform the bias correction of the measured data.

The exercise analysis unit 211 defines an exercise analysis model (double pendulum model) in which body information (the height of the user 2 (the length of an arm)), club specification information (the length or a central position of the shaft), the sensor-mounted position information (the distance from the grip end), features (a rigidity body and the like) of the golf club 3, body features (for example, a direction in which a joint is bent is decided) are considered, and then calculates a trajectory of the golf club 3 in a swing of the user 2 using the exercise analysis model and the information regarding the position and attitude of the sensor unit 10.

The exercise analysis unit 211 detects a timing (a timing of an impact) at which hitting is performed for a period of a swing motion of the user 2 using measured data and time information stored in the storage unit 24. For example, the exercise analysis unit 211 calculates a resultant value of the measured data (the acceleration data or the angular velocity data) output by the sensor unit 10 and specifies a timing (a time) at which the user 2 hits a ball based on the resultant value.

The exercise analysis unit 211 also generates information regarding a head speed from backswing to follow-through, an incident angle (club path) or a face angle at the time of hitting, shaft rotation (a change amount of a face angle during a swing), a deceleration rate of the golf club 3, and the like or information regarding a variation in each piece of information in a case in which the user 2 performs a swing a plurality of times using the exercise analysis model and the information regarding the position and attitude of the sensor unit 10.

The exercise analysis unit 211 detects a series of motions (also referred to as a "rhythm") from start to end of a swing, for example, start of a swing, a backswing, a top, a downswing, an impact, follow-through, and end of the swing, using the measured data acquired from the sensor unit 10. A specific detection procedure of the rhythm is not particularly limited. For example, the following procedure can be adopted.

First, the exercise analysis unit 211 calculates a sum (referred to as a norm) of the magnitudes of angular velocities around an axes at times t using the angular velocity data at the acquired times t. The exercise analysis unit 211 may differentiate the norm of the angular velocity at each time t by time.

Figure 4:
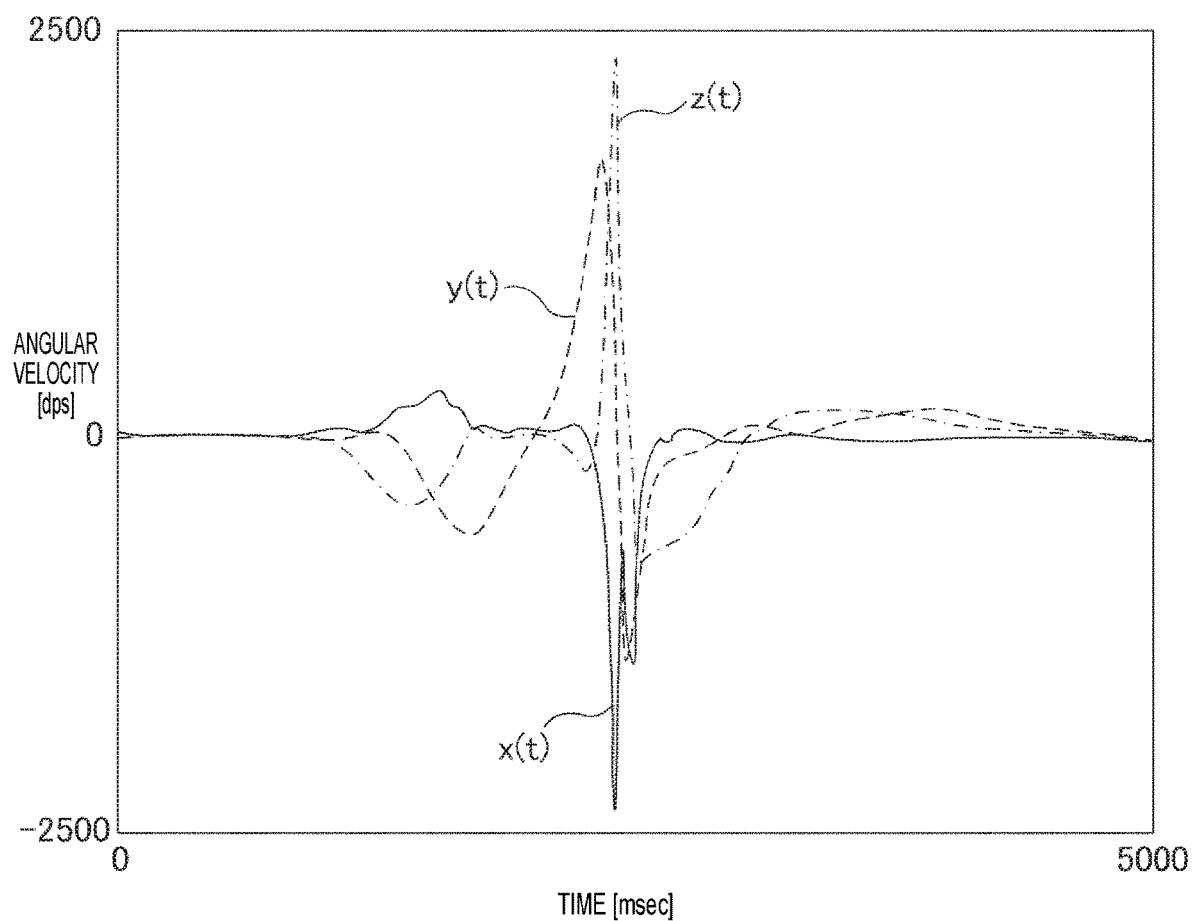
FIG. 4 is a diagram illustrating an example of an angular velocity output from a sensor unit.
Figure 5:
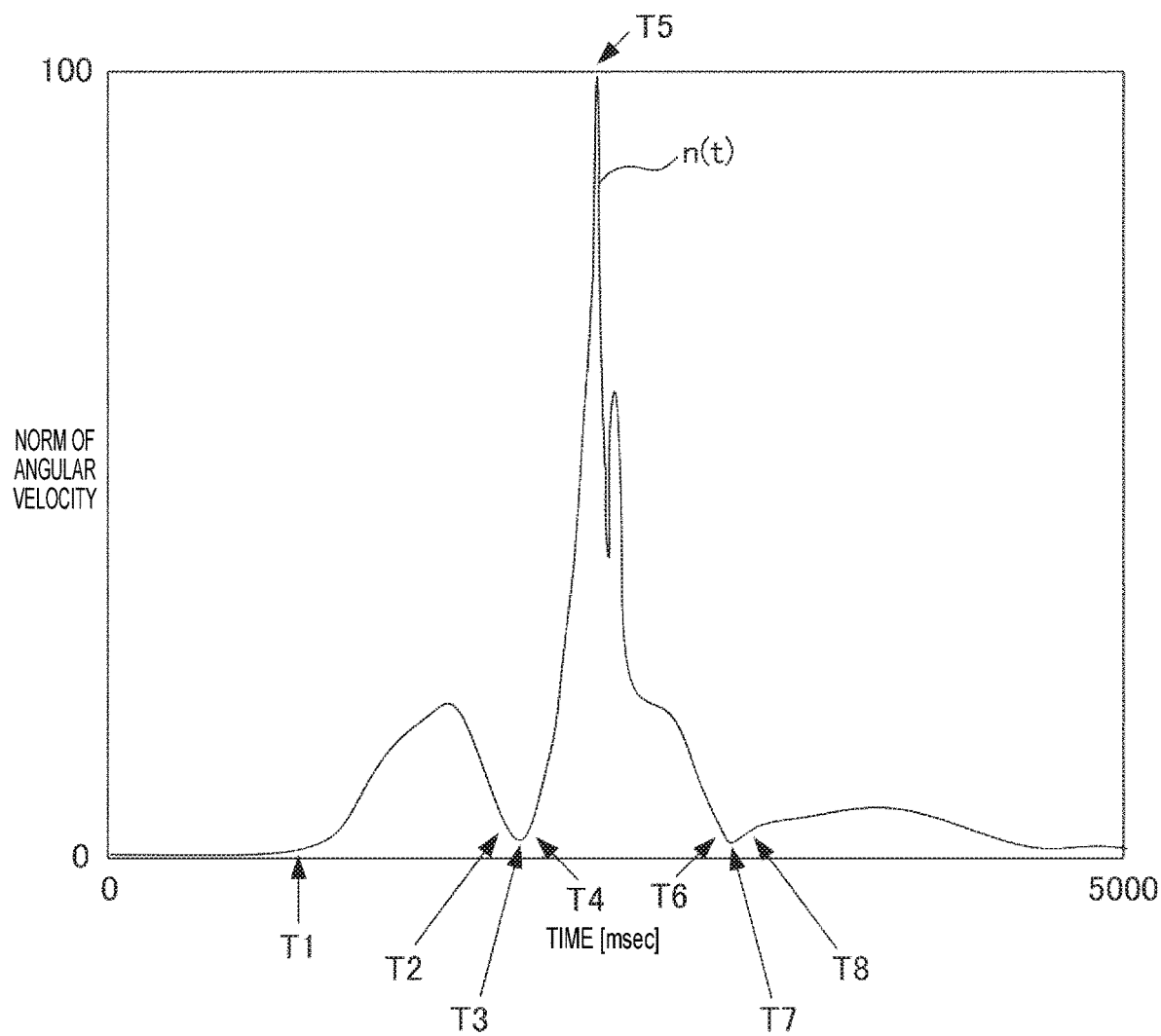
FIG. 5 is a diagram illustrating an example of a norm of an angular velocity.
Figure 6:
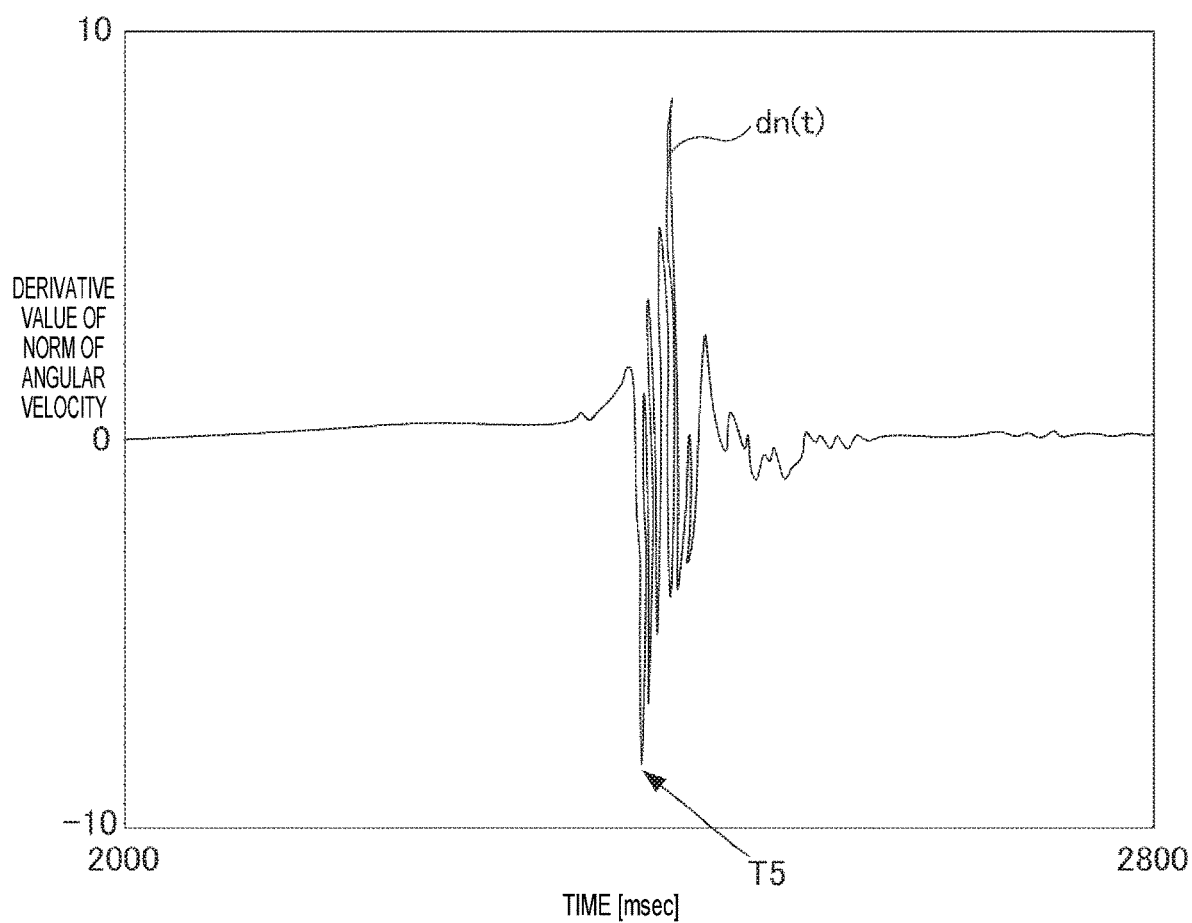
FIG. 6 is a diagram illustrating an example of a derivative value of the norm of an angular velocity.

Here, a case will be considered in which angular velocities around three axes (x, y, and z axes) are shown in, for example, a graph illustrated in FIG. 4 (which is a diagram illustrating an example of an angular velocity output from the sensor unit). In FIG. 4, the horizontal axis represents a time (msec) and the vertical axis represents an angular velocity (dps). The norm of the angular velocity is indicated in, for example, a graph illustrated in FIG. 5 (which is a diagram illustrating an example of the norm of the angular velocity). In FIG. 5, the horizontal axis represents a time (msec) and the vertical axis represents the norm of the angular velocity. A derivative value of the norm of the angular velocity is indicated in, for example, a graph illustrated in FIG. 6 (which is a diagram illustrating an example of a derivative value of the norm of the angular velocity). In FIG. 6, the horizontal axis represents a time (msec) and the vertical axis represents a derivative value of the norm of the angular velocity. FIGS. 4 to 6 are illustrated to easily understand the embodiment and do not indicate accurate values.

The exercise analysis unit 211 detects a timing of an impact in a swing using the calculated norm of the angular velocity. For example, the exercise analysis unit 211 detects a timing at which the norm of the angular velocity is the largest as the timing of the impact (T5 of FIG. 5). For example, the exercise analysis unit 211 may detect the former timing between timings at which the derivative value of the calculated norm of the angular velocity is the largest and is the smallest as the timing as the impact (T5 of FIG. 6).

For example, the exercise analysis unit 211 detects a timing at which the calculated norm of the angular velocity is the minimum as a timing of a top of the swing before the impact (T3 of FIG. 5). For example, the exercise analysis unit 211 specifies a period in which the norm of the angular velocity is continuously equal to or less than a first threshold before the impact as a top period (a period of accumulation at the top) (T2 to T4 of FIG. 5).

For example, the exercise analysis unit 211 detects a timing at which the norm of the angular velocity is equal to or less than a second threshold before the top as a timing of start of the swing (T1 of FIG. 5).

For example, the exercise analysis unit 211 detects a timing at which the norm of the angular velocity is the minimum after the impact as a timing of end (finishing) of the swing (T7 of FIG. 5). For example, the exercise analysis unit 211 may detect a first timing at which the norm of the angular velocity is equal to or less than a third threshold after the impact as a timing of end (finishing) of the swing. For example, the exercise analysis unit 211 specifies a period in which the norm of the angular velocity is equal to or less than a fourth threshold so as to be close to the timing of the impact and after the timing of the impact as a finishing period (T6 to T8 of FIG. 5).

In this way, the exercise analysis unit 211 can detect a rhythm of the swing. The exercise analysis unit 211 can specify the periods (for example, a backswing period from the start of the swing to the start of the top, a downswing period from the end of the top to the impact, and a follow-through period from the impact to the end of the swing) during the swing by detecting the rhythm.

Referring back to FIG. 3, the description will be made. The calculation unit 212 calculates a deviation amount (a distance from a standard line to a hitting position) of the hitting position from the standard line (equivalent to a standard position according to the invention) set on the hitting surface 3*c* based on the angular velocity around the major axis of the shaft portion 3*a* at the time of the impact. For example, as will be described below, the storage unit 24 stores information indicating a relation between the angular velocity around the major axis of the golf club 3 and the deviation amount of the hitting position (hereinafter referred to as relation information) in advance. With reference to the relation information stored in the storage unit 24, the calculation unit 212 calculates the deviation amount of the hitting position from the standard line set on the hitting surface 3*c*. The angular velocity around the major axis of the shaft portion 3*a* is acquired by the sensor information acquisition unit 210, as described above. The timing of the impact is detected by the exercise analysis unit 211, as described above.

It is recognized that an angular velocity around the major axis of the shaft portion 3*a* and a deviation in a hitting position of a ball from a sweet spot have the correlation, as described in FIG. 2. Accordingly, for example, the relation information can be indicated as an expression in which an angular velocity around the major axis of the shaft portion 3*a* is an independent variable and a deviation amount of the hitting position from the standard line (for example, a sweet spot) set on the hitting surface 3*c* is a dependent variable. That is, for example, the calculation unit 212 can calculate the deviation amount (the dependent variable) of the hitting position from the standard line set on the hitting surface 3*c* by substituting the angular velocity around the major axis of the shaft portion 3*a* at the time of the impact acquired by the sensor information acquisition unit 210 into the independent variable of the relation information.

For example, the relation information is acquired in advance, for example, before shipment of the exercise analysis system 1 and is stored in the storage unit 24. For example, an acquirer (for example, a manufacturer that manufactures the exercise analysis system 1) acquiring the relation information can acquire the relation information by wearing the sensor unit 10 on the golf club 3, swing the golf club 3, and hits a ball on the hitting surface 3*c*.

Specifically, the acquirer swings the golf club 3 and hits a ball on the hitting surface 3*c* and measures an angular velocity around the major axis of the shaft portion 3*a* at the time of an impact. For example, the acquirer can measure an angular velocity around the major axis of the shaft portion 3*a* at the time of an impact using the exercise analysis device 20.

The acquirer measures a deviation amount of a hitting position from the standard line set on the hitting surface 3*c* when the acquirer hits a ball on the hitting surface 3*c*. For example, the acquirer applies a marker or the like in which a trace remains at the time of hitting the ball on the hitting surface 3*c* of the golf club 3 and measures a deviation amount of a hitting position from the standard line set on the hitting surface 3*c* of the golf club 3.

The standard line set on the hitting surface 3*c* is assumed to be, for example, a sweet spot of the hitting surface 3*c*. In this case, the acquirer measures the deviation amount of the hitting position from the sweet spot when the acquirer hits the ball on the hitting surface 3*c*. Specifically, the acquirer measures the hitting position with respect to the origin of the h axis in FIG. 2. Thus, the calculation unit 212 can calculate the deviation amount of the hitting position from the sweet spot of the hitting surface 3*c*. Of course, the standard line may be set to a portion other than the sweet spot.

Figure 7:
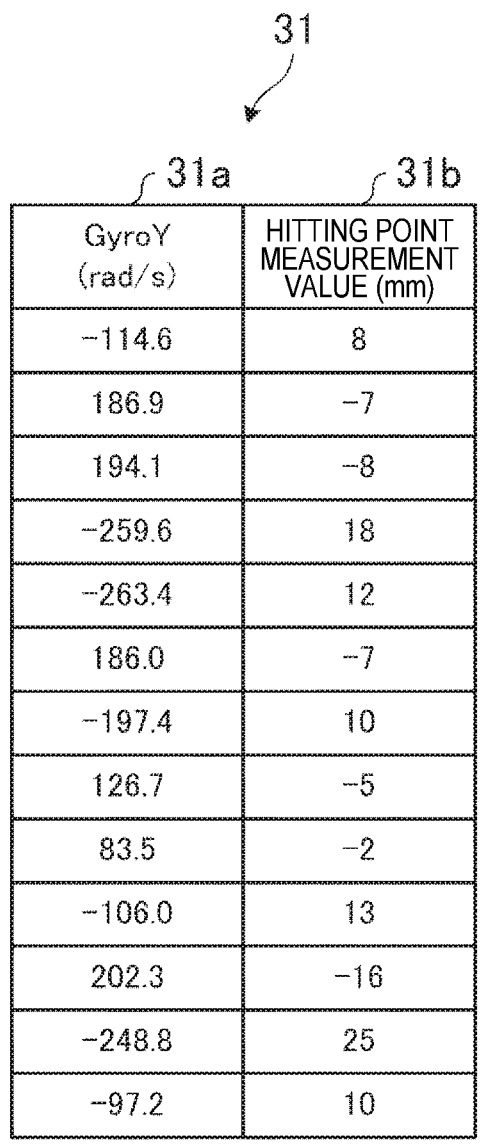
FIG. 7 is a diagram illustrating an example of relation information.

FIG. 7 is a diagram illustrating an example of the relation information. As illustrated in FIG. 7, relation information 31 includes GyroY 31a and a hitting point measurement value 31b. For example, the relation information 31 is acquired in advance by the acquirer in accordance with the above-described method.

GyroY 31a is an angular velocity around the major axis of the shaft portion 3a at the time of an impact.

The hitting point measurement value 31b is a deviation amount of the hitting position from the sweet spot in the horizontal direction of the hitting surface 3c.

For example, in the case of the relation information 31 in FIG. 7, it can be understood that a deviation amount of a hitting position from the sweet spot is "8 (mm)" when GyroY 31a is "−114.6 (rad/s)". Specifically, when the shaft portion 3a of the golf club 3 illustrated in FIG. 2 is rotated in an opposite direction to a direction indicated by the arrow A2 at an angular velocity of "114.6 (rad/s)", it can be understood that the deviation amount of the hitting position from the sweet spot indicated by the one-dot chain line A1 is "h=+8 (mm)".

Figure 8:
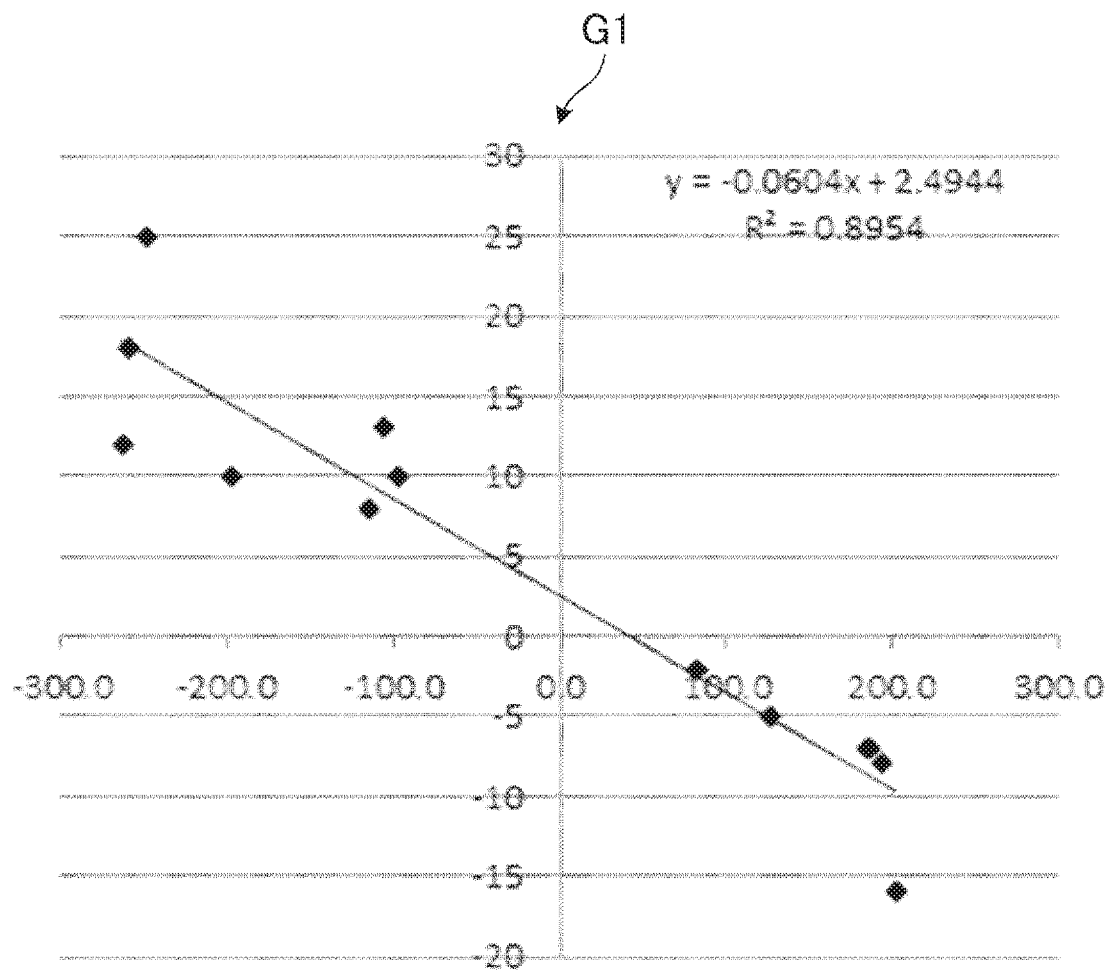
FIG. 8 is a graph diagram illustrating an example of the relation information of FIG. 7.

FIG. 8 is a graph diagram illustrating an example of the relation information of FIG. 7. The horizontal axis of a graph G1 illustrated in FIG. 8 represents an angular velocity. The vertical axis of the graph G1 represents a deviation amount of a hitting position. Black rhombuses in the graph G1 plot GyroY 31a and the hitting point measurement values 31b of the relation information 31 in FIG. 7 on the graph G1.

The correlation of GyroY 31a and the hitting point measurement values 31b is recognized as illustrated in FIG. 8. This relation is indicated as a linear expression. A coefficient and an interception of the linear expression can be obtained by regression analysis. In the case of FIG. 8, the linear expression is indicated in Expression (1) below.

$$y = -0.0604x + 2.4944 \qquad (1)$$

A contribution ratio is "$R^2 = 0.8954$".

For example, Expression (1) is calculated in advance by the foregoing acquirer and is stored in the storage unit 24. Thus, referring to the storage unit 24, the calculation unit 212 can calculate the deviation amount of the hitting position from the sweet spot when the user 2 swings the golf club 3.

For example, the calculation unit 212 can calculate a deviation amount "y" from the sweet spot by substituting an angular velocity around the major axis of the shaft portion 3a at the time of an impact into "x" of Expression (1) stored in the storage unit 24 when the user 2 hits a ball with the golf club 3.

Referring back to FIG. 3, the description will be made. The image generation unit 213 performs a process of generating image data including information regarding the deviation amount from the sweet spot.

The output processing unit 214 performs a process of displaying various images (including letters or signs in addition to images corresponding to the image data generated by the image generation unit 213) on the display unit 25. For example, the output processing unit 214 causes the display unit 25 to display an image corresponding to the image data generated by the image generation unit 213 automatically or in response to an input manipulation by the user 2 after the swing motion of the user 2 ends. Alternatively, the sensor unit 10 may include a display unit and the output processing unit 214 may transmit image data to the sensor unit 10 via the communication unit 22 and cause the display unit of the sensor unit 10 to display various images.

The output processing unit 214 performs a process of causing the audio output unit 26 to output various kinds of audio (including voice or a buzzer sound). For example, the output processing unit 214 may read various kinds of information stored in the storage unit 24 and cause the audio output unit 26 to output an audio or voice for exercise analysis automatically or at the time of performing a predetermined input manipulation after the swing motion of the user 2 ends. Alternatively, the sensor unit 10 may include an audio output unit and the output processing unit 214 may transmit various kinds of audio data or voice data to the sensor unit 10 via the communication unit 22 and cause the audio output unit of the sensor unit 10 to output various kinds of audio or voice.

The exercise analysis device 20 or the sensor unit 10 may include a vibration mechanism and various kinds of information may be converted into vibration information by the vibration mechanism to be presented to the user 2.

Figure 9:
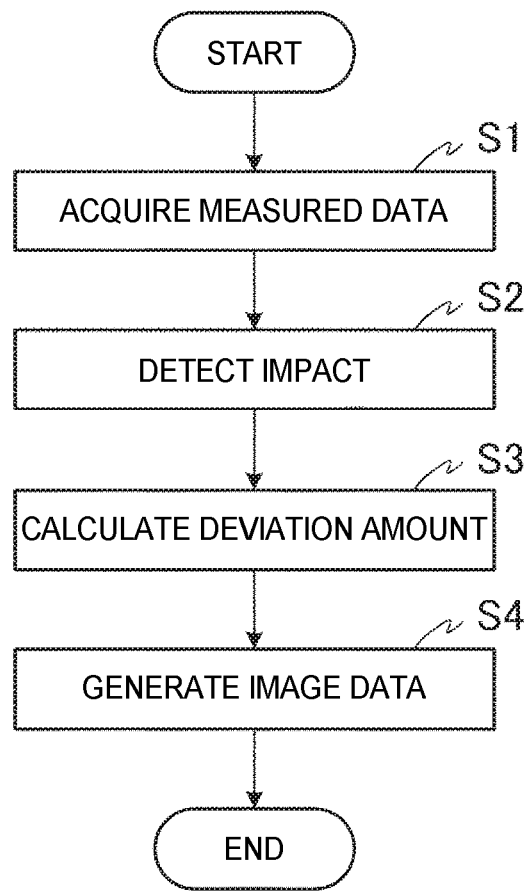
FIG. 9 is a flowchart illustrating an example of an operation of an exercise analysis device.

FIG. 9 is a flowchart illustrating an example of an operation of the exercise analysis device. For example, the exercise analysis device 20 performs a process of the flowchart of FIG. 9 when the user 2 swings the golf club 3. The storage unit 24 is assumed to store the relation information indicated in Expression (1) in advance.

First, the sensor information acquisition unit 210 acquires measured data of the sensor unit 10 (step S1). The measured data includes an angular velocity around the major axis of the shaft portion 3a. The control unit 21 may perform processes subsequent to step S2 in real time when first measured data in the swing motion (also including a standstill motion) of the user 2 is acquired, or may perform the processes subsequent to step S2 after some or all of the series of measured data in the swing motion of the user 2 are acquired from the sensor unit 10.

Next, the exercise analysis unit 211 detects a timing of an impact of the golf club 3 (step S2).

Next, the calculation unit 212 acquires an angular velocity around the major axis of the shaft portion 3a at the time of an impact based on the angular velocity around the major axis of the shaft portion 3a acquired in step S1 and the timing of the impact detected in step S2. Then, the calculation unit 212 calculates a deviation amount (distance) of the hitting position from the sweet spot set on the hitting surface 3c based on the acquired angular velocity around the major axis of the shaft portion 3a at the time of the impact (step S3). For example, the calculation unit 212 calculates the deviation amount of the hitting position substituting the acquired angular velocity around the major axis of the shaft portion 3a at the time of the impact into the independent variable of Expression (1) stored in the storage unit 24.

The image generation unit 213 generates image data including the information regarding the deviation amount calculated in step S3 (step S4). Thus, the image data generated by the image generation unit 213 is displayed on the display unit 25 by the output processing unit 214, and the user 2 can ascertain the deviation amount of the hitting position from the sweet spot.

Figure 10:
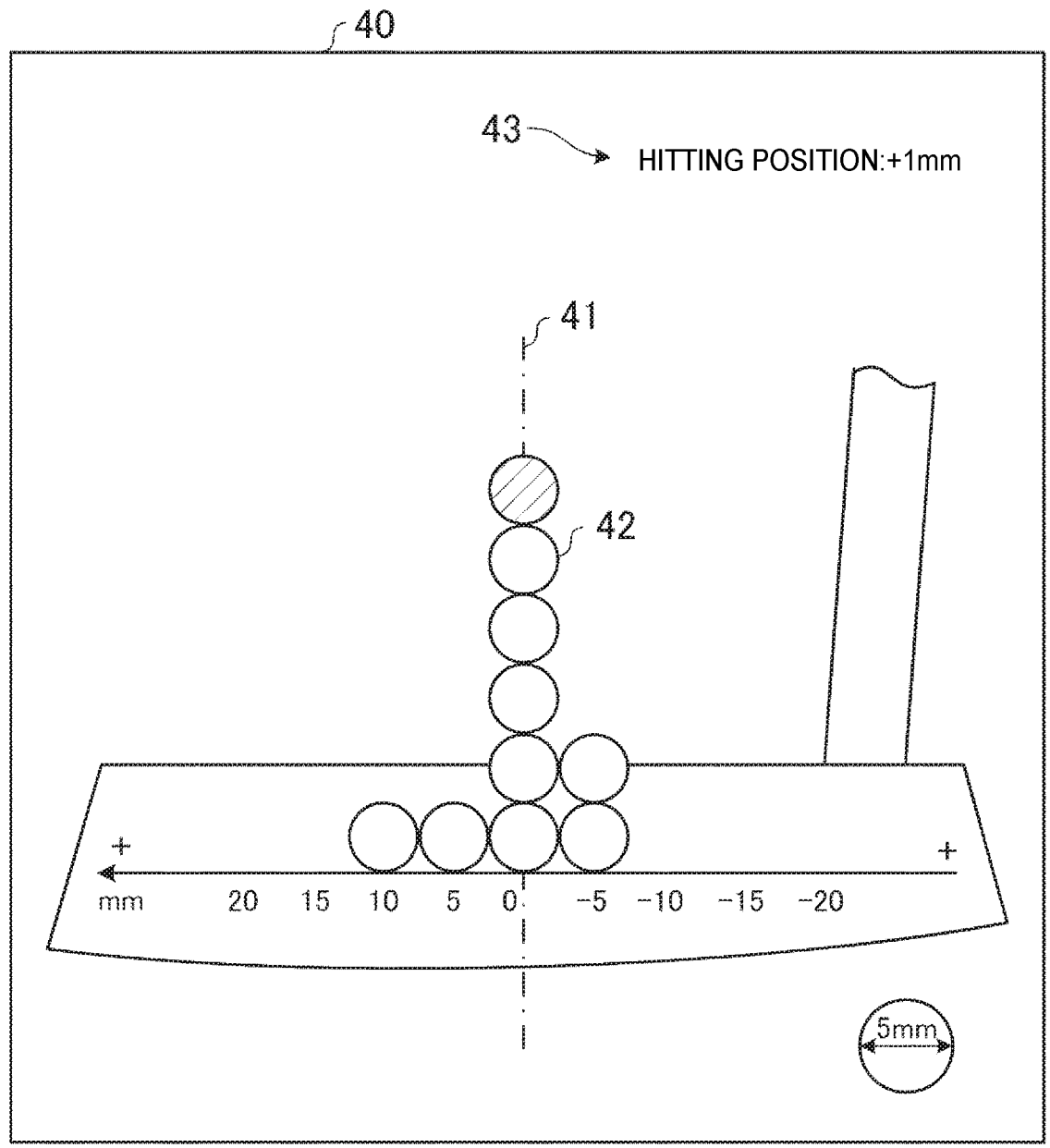
FIG. 10 is a diagram illustrating an example of a screen displayed on a display unit.

FIG. 10 is a diagram illustrating an example of a screen displayed on a display unit. The image data generated by the image generation unit 213 is output to the display unit 25 by the output processing unit 214. A screen 40 illustrated in FIG. 10 is shown in a screen displayed on the display unit 25.

An image resembling a part of the golf club 3 is displayed in the screen 40. In the example of the screen 40, the golf club 3 is a putter.

A one-dot chain line 41 shown in the screen 40 indicates a sweet spot of the golf club 3.

Circles 42 shown in the screen 40 indicate a histogram of hitting positions of a ball. A diameter of one circle 42 in the horizontal direction indicates the width of a hitting position of the ball. In the case of the screen 40, the diameter indicates the width of "5 mm".

The number of circles 42 in the vertical direction indicates a frequency of the hitting position of the ball. For example, in the case of the example of the screen 40, it can be understood that a frequency of the hitting position "−5±2.5 (mm)" is "twice".

The circle 42 indicated by oblique lines indicates the recent hitting position of the ball. In the case of the example of the screen 40, the hitting position of the recent ball is "+1 mm". Therefore, the circle 42 indicated by the oblique lines is displayed at a scale of "0±2.5 (mm)".

A hitting position 43 of the screen 40 indicates the recent hitting position of the ball. In the case of the example of the screen 40, it can be understood that the recent hitting position is deviated by "+1 mm" from the sweet spot.

In this way, the sensor information acquisition unit 210 of the exercise analysis device 20 acquires an angular velocity around the major axis of the shaft portion 3a of the golf club 3 generated in a swing. The exercise analysis unit 211 detects a timing of an impact of the golf club 3. Then, the calculation unit 212 calculates a deviation amount of the hitting position from the standard line set on the hitting surface 3c of the golf club 3 based on the angular velocity at the time of the impact.

Thus, the user 2 can ascertain the deviation of the hitting position from the standard line set on the hitting surface 3c of the golf club 3.

Since the user 2 can ascertain a deviation in a hitting position from the standard line set on the hitting surface 3c of the golf club 3, a swing technique can be improved.

The image generation unit 213 generates image data in which the hitting position of the ball is displayed as a histogram. Thus, the user 2 can simply ascertain where the ball is hit on the hitting surface 3c of the golf club 3 in past and recent swings.

As described above, the storage unit 24 stores the relation information indicated in the linear expression in advance, but the invention is not limited thereto. For example, the acquirer may store the relation information 31 illustrated in FIG. 7 in the storage unit 24. Then, the calculation unit 212 may acquire a deviation amount close to the angular velocity acquired by the sensor information acquisition unit 210 from the storage unit 24, perform a complementing process, and calculate a deviation amount of the hitting position.

As described above, the relation information is stored in the storage unit 24 before shipment of the exercise analysis system 1, but the invention is not limited thereto. For example, the exercise analysis device 20 may download the relation information from a site or the like of a manufacturer after shipment and store the relation information in the storage unit 24.

As described above, the acceleration sensor 13 and the angular velocity sensor 14 are contained and integrated in the sensor unit 10, but the acceleration sensor 13 and the angular velocity sensor 14 may not be integrated. Alternatively, the acceleration sensor 13 and the angular velocity sensor 14 may not be contained in the sensor unit 10, but may be mounted directly on the golf club 3 or the user 2. As described above, the sensor unit 10 and the exercise analysis device 20 are separated, but these units may be integrated to be mounted on the golf club 3 or the user 2. [0105]

The sensor unit 10 may include a light-emitting unit such as an LED. Then, the output processing unit 214 may output a calculation result of the calculation unit 212 to the light-emitting unit. For example, the output processing unit 214 is configured to emit a first color such as green from the light-emitting unit in a case in which a deviation amount of a hitting position is within a predetermined range (for example, ±2.5 (mm)) from the sweet spot. The output processing unit 214 is configured to emit a second color such as red from the light-emitting unit in a case in which a deviation amount of a hitting position is greater than a predetermined range (greater than, for example, +2.5 (mm)) from the sweet spot. The output processing unit 214 is configured to emit a third color such as blue from the light-emitting unit in a case in which a deviation amount of a hitting position is less than a predetermined range (less than, for example, −2.5 (mm)) from the sweet spot.

The sensor unit 10 may includes an audio output unit such as a speaker. Then, the output processing unit 214 may output a calculation result of the calculation unit 212 as audio from the audio output unit.

Second Embodiment

Next, a second embodiment will be described with reference to the drawings. In the second embodiment, content of relation information is different from that of the first embodiment. For example, in the second embodiment, the storage unit 24 in advance stores relation information indicating a relation between information (value) obtained by dividing the angular velocity of the shaft portion 3a by a speed of the hitting portion 3b and a deviation amount of a hitting position. Then, the calculation unit 212 divides an angular velocity at the time of an impact acquired by the sensor information acquisition unit 210 by a speed of the hitting portion 3b at the time of the impact and calculates a deviation amount of the hitting position with reference to the storage unit 24 based on a value obtained through the division. Hereinafter, differences from the first embodiment will be described.

FIG. 11 is a diagram illustrating an example of relation information according to the second embodiment. As illustrated in FIG. 11, relation information 51 includes GyroY 51a, a head speed (HS) 51b, GyroY/HS 51c, and a hitting point measurement value 51d.

GyroY 51a is an angular velocity around the major axis of the shaft portion 3a at the time of an impact. For example, GyroY 51a is acquired in advance by an acquirer as in the first embodiment.

HS 51b is a speed of the hitting portion 3b at the time of an impact. HS 51b is acquired in advance by the acquirer as in GyroY 51a. For example, the acquirer can acquire HS 51b using the exercise analysis device 20.

The exercise analysis unit 211 can calculate a head speed from a backswing to follow-through using an exercise analysis model and information regarding a position and an attitude of the sensor unit 10, as described in the first embodiment. That is, the exercise analysis unit 211 can calculate a speed of the hitting portion 3b at the time of the impact.

GyroY/HS 51c is a value obtained by dividing GyroY 51a by HS 51b.

The hitting point measurement value 51d is a deviation amount of a hitting position from the sweet spot in the horizontal direction of the hitting surface 3c. The hitting point measurement value 51d is acquired in advance using a marker or the like by the acquirer, as in the first embodiment.

Figure 12:
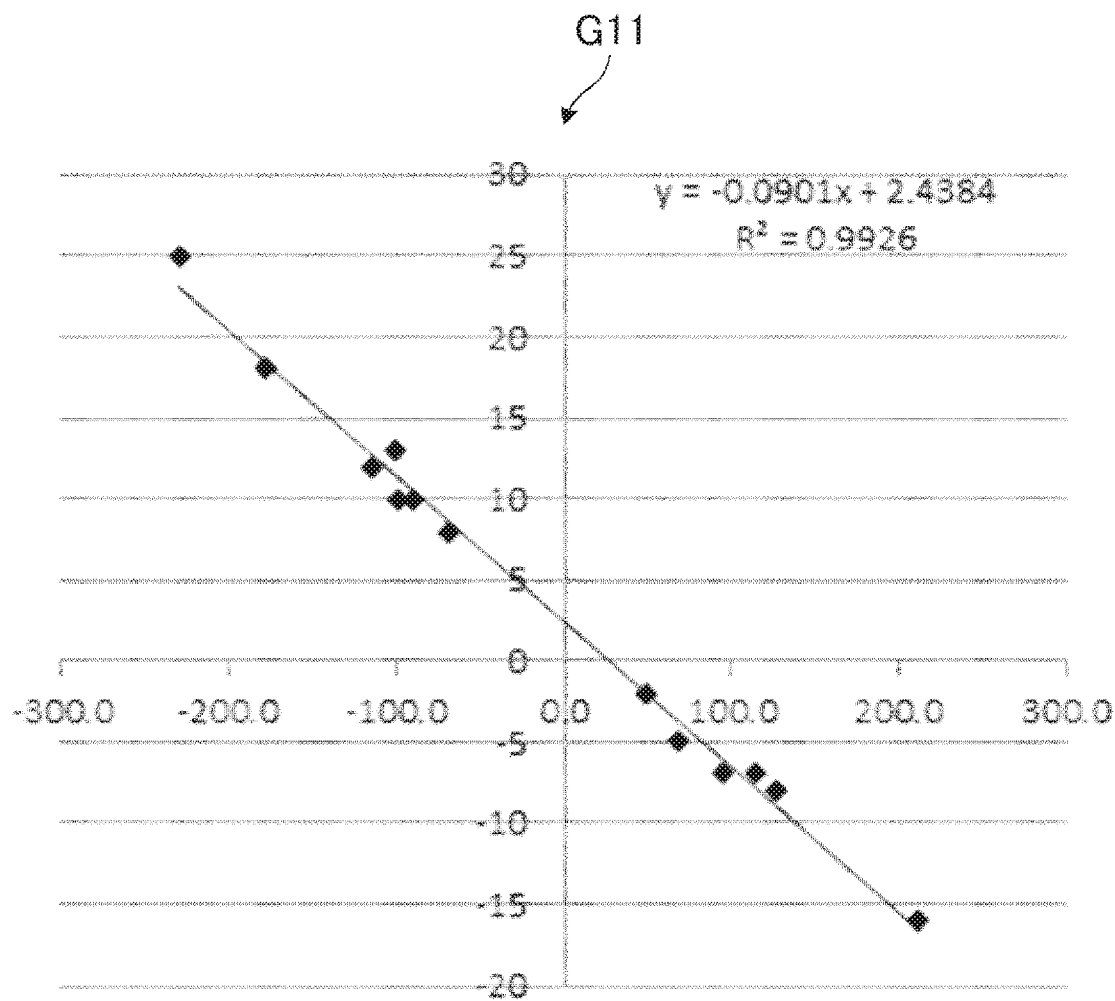
FIG. 12 is a graph diagram illustrating an example of the relation information of FIG. 11.

FIG. 12 is a graph diagram illustrating an example of the relation information of FIG. 11. The horizontal axis of a graph G11 illustrated in FIG. 12 represents a value obtained by dividing an angular velocity by a head speed. The vertical axis of the graph G11 represents a deviation amount of a hitting position. Black rhombuses in the graph G11 plot GyroY/HS 51c and the hitting point measurement value 51d of the relation information 51 in FIG. 11 on the graph G11.

As indicated in the graph G11, it is recognized that GyroY/HS 51c and the hitting point measurement value 51d have correlation, and the correlation is indicated in a linear expression. A coefficient and an interception of the linear expression can be obtained by regression analysis. In the case of the example of FIG. 12, the linear expression is indicated in Expression (2) below.

$$y = -0.0901x + 2.4384 \quad (2)$$

A contribution ratio is "$R^2=0.9926$".

Expression (2) is calculated in advance by the acquirer and is stored in the storage unit 24, as in the first embodiment. Thus, referring to the storage unit 24, the calculation unit 212 can calculate the deviation amount of the hitting position from the sweet spot when the user 2 swings the golf club 3.

For example, the calculation unit 212 divides an angular velocity around the major axis of the shaft portion 3a at the time of an impact by a speed of the hitting portion 3b at the time of the impact when the user 2 hits a ball with the golf club 3. Then, the calculation unit 212 can calculate a deviation amount from the sweet spot by substituting the value obtained by dividing the angular velocity by the speed into "x" of Expression (2) stored in the storage unit 24. The speed of the hitting portion 3b at the time of an impact is calculated by the exercise analysis unit 211, as described in the first embodiment.

Here, the contribution ratio of Expression (1) according to the first embodiment is "$R^2=0.8954$" and the contribution ratio of Expression (2) according to the second embodiment is "$R^2=0.9926$". Accordingly, the correlation between GyroY/HS 51c in which the angular velocity is divided by the speed and the hitting point measurement value 51d can be said to be stronger than the correlation of GyroY 31a and the hitting point measurement value 31b described in the first embodiment.

That is, the calculation unit 212 can calculate a more accurate deviation amount by calculating a deviation amount of the hitting position using the relation information indicated in Expression (2). It is considered that the reason why the correlation between GyroY/HS 51c and the hitting point measurement value 51d is stronger than the correlation of GyroY 31a and the hitting point measurement value 31b is that the angular velocity around the major axis of the shaft portion 3a and the speed of the hitting portion 3b at the time of an impact have a proportional relation.

In this way, the relation information indicates a relation between the deviation amount of the hitting position and the value obtained by dividing the angular velocity around the major axis of the shaft portion 3a by the speed of the hitting portion 3b. Then, the calculation unit 212 divides the angular velocity around the major axis of the shaft portion 3a at the time of the impact by the speed of the hitting portion 3b at the time of the impact and calculates the deviation amount of the hitting position with reference to the relation information based on the value obtained through the division.

Thus, the exercise analysis device 20 can calculate a more accurate deviation amount of the hitting position.

The user 2 can ascertain a deviation in the hitting position from the standard line set on the hitting surface 3c of the golf club 3 more accurately.

The exercise analysis unit 211 may calculate the speed of the hitting portion 3b at the time of the impact in accordance with a general method other than the foregoing method. For example, the exercise analysis unit 211 may obtain the speed from an angular velocity of a swing axis perpendicular to a swing plane of the shaft portion 3a and the distance between the swing axis and the hitting portion 3b.

Third Embodiment

Next, a third embodiment will be described with reference to the drawings. The relation information is changed in accordance with the type of golf club 3 (equivalent to a shape according to the invention). For example, as a putter, there are a pin type, a mallet type, and a neomallet type. The relation information differs according to each type. In the third embodiment, the relation information according to the type of golf club 3 is stored in the storage unit 24 and relation information for calculating a deviation amount of a hitting position is switched according to the type of golf club 3 used by the user 2. Hereinafter, differences from the first and second embodiments will be described.

Figures 13, 14:
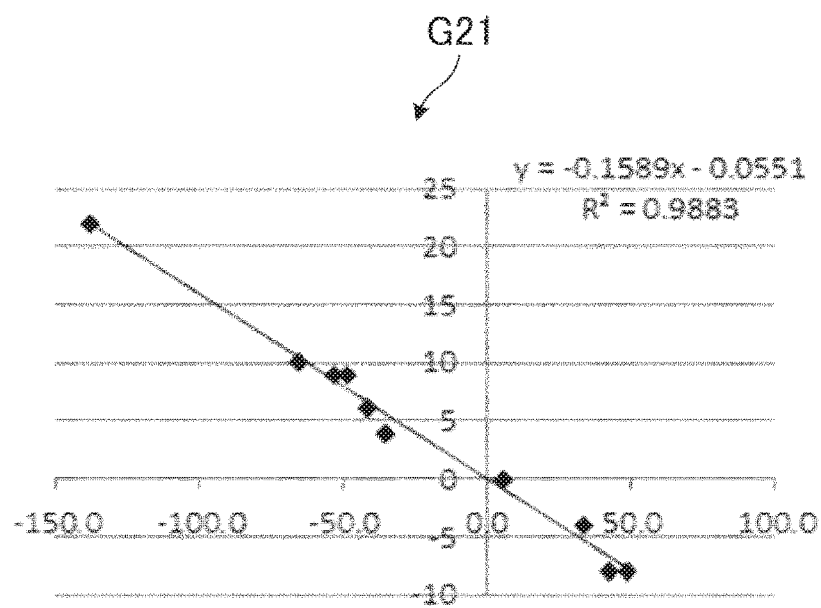
FIG. 13 is a diagram illustrating an example of relation information according to a third embodiment.
FIG. 14 is a graph diagram illustrating an example of the relation information of FIG. 13.

FIG. 13 is a diagram illustrating an example of relation information according to the third embodiment. Relation information 61 illustrated in FIG. 13 indicates relation information in a case in which the golf club 3 is of a neomallet type. The relation information 61 includes GyroY 61a, HS 61b, GyroY/HS 61c, and a hitting point measurement value 61d.

GyroY 61a, HS 61b, GyroY/HS 61c, and the hitting point measurement value 61d are the same as GyroY 51a, HS 51b, GyroY/HS 51c, and the hitting point measurement value 51d in FIG. 11, and thus the description thereof will be omitted. GyroY 51a, HS 51b, GyroY/HS 51c, and the hitting point measurement value 51d in FIG. 11 indicate relation information in a case in which the golf club 3 is of a pin type.

FIG. 14 is a graph diagram illustrating an example of the relation information of FIG. 13. The horizontal axis of a graph G21 illustrated in FIG. 14 represents a value obtained by dividing an angular velocity by a head speed. The vertical axis of the graph G21 represents a deviation amount of a hitting position. Black rhombuses in the graph G21 plot GyroY/HS 61c and the hitting point measurement value 61d of the relation information 61 in FIG. 13 on the graph G21.

As indicated in the graph G21, it is recognized that GyroY/HS 61c and the hitting point measurement value 61d of the neomallet type of golf club 3 have correlation, and the correlation is indicated in a linear expression. A coefficient and an interception of the linear expression can be obtained by regression analysis. In the case of FIG. 14, the linear expression is indicated in Expression (3).

$$y = -0.1589x - 0.0551 \quad (3)$$

A contribution ratio is "$R^2=0.9883$".

Expression (3) is stored in advance in the storage unit 24, as in each of the embodiments. Thus, referring to the storage unit 24, the calculation unit 212 can calculate the deviation amount of the hitting position from the sweet spot when the user 2 swings the neomallet type of golf club 3.

Figure 15:
FIG. 15 is a diagram illustrating an example of another type of relation information.

FIG. 15 is a diagram illustrating an example of another type of relation information. Relation information 71 illustrated in FIG. 15 indicates relation information in a case in which the golf club 3 is of a mallet type. The relation information 71 includes GyroY 71*a*, HS 71*b*, GyroY/HS 71*c*, and a hitting point measurement value 71*d*.

GyroY 71*a*, HS 71*b*, GyroY/HS 71*c*, and the hitting point measurement value 71*d* are the same as GyroY 61*a*, HS 61*b*, GyroY/HS 61*c*, and the hitting point measurement value 61*d* in FIG. 13, and thus the description thereof will be omitted.

Figure 16:
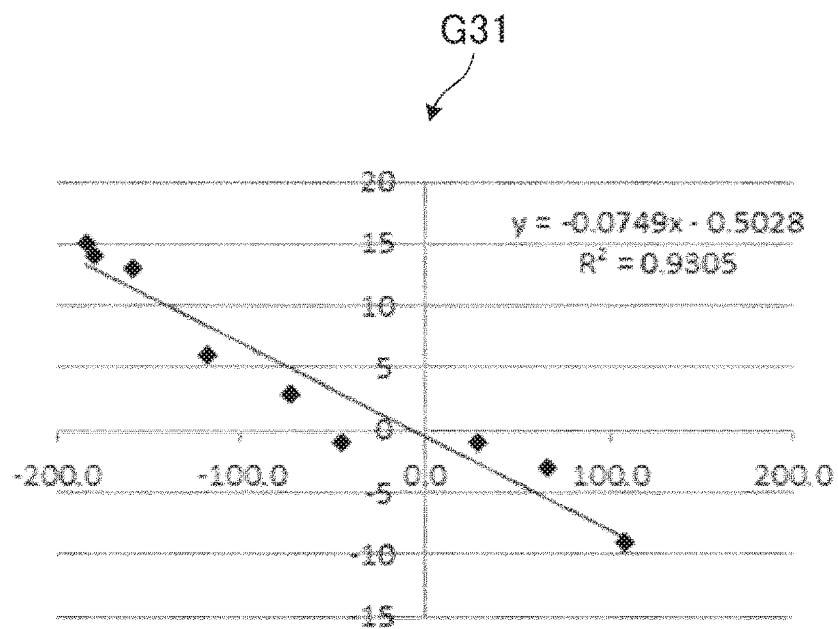
FIG. 16 is a graph diagram illustrating an example of the relation information of FIG. 15.

FIG. 16 is a graph diagram illustrating an example of the relation information of FIG. 15. The horizontal axis of a graph G31 illustrated in FIG. 16 represents a value obtained by dividing an angular velocity by a head speed. The vertical axis of the graph G31 represents a deviation amount of a hitting position. Black rhombuses in the graph G31 plot GyroY/HS 71*c* and the hitting point measurement value 71*d* of the relation information 71 in FIG. 15 on the graph G31.

As indicated in the graph G31, it is recognized that GyroY/HS 71*c* and the hitting point measurement value 71*d* of the mallet type of golf club 3 have correlation, and the correlation is indicated in a linear expression. A coefficient and an interception of the linear expression can be obtained by regression analysis. In the case of the example of FIG. 16, the linear expression is indicated in Expression (4) below.

$$y = -0.0749x - 0.5028 \quad (4)$$

A contribution ratio is "$R^2 = 0.9305$".

Expression (4) is stored in advance in the storage unit 24, as in each of the foregoing embodiments. Thus, referring to the storage unit 24, the calculation unit 212 can calculate the deviation amount of the hitting position from the sweet spot when the user 2 swings the mallet type of golf club 3.

Figure 17:
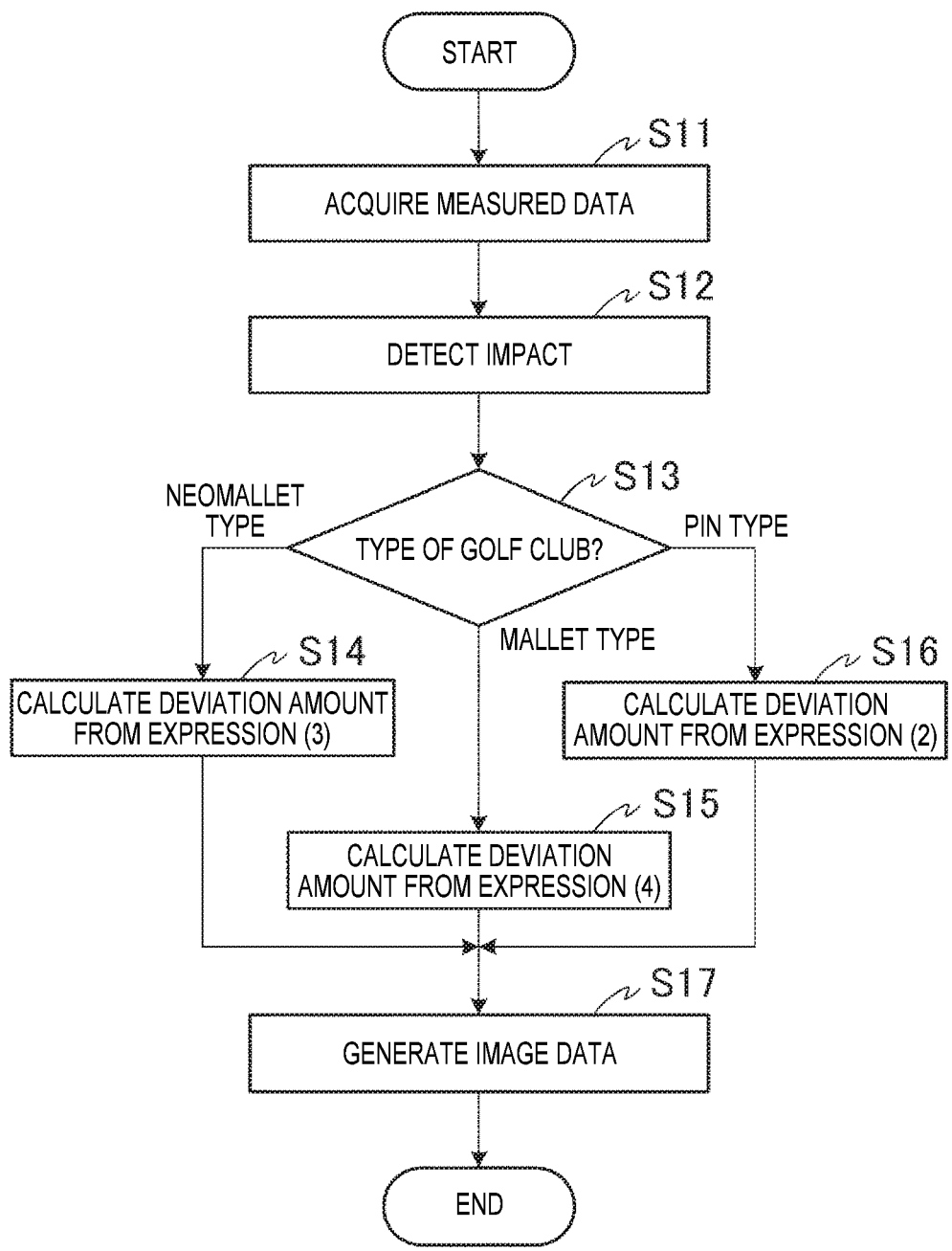
FIG. 17 is a flowchart illustrating an example of an operation of an exercise analysis device.

FIG. 17 is a flowchart illustrating an example of an operation of an exercise analysis device. For example, when the user 2 swings the golf club 3, the exercise analysis device 20 performs a process of the flowchart of FIG. 17. The storage unit 24 is assumed to store the relation information indicated in Expressions (2), (3), and (4) in advance. The manipulation unit 23 is assumed to receive the type of golf club 3 used by the user 2 from the user 2. The manipulation unit 23 stores, for example, the type of golf club 3 received from the user 2 in the storage unit 24.

First, the sensor information acquisition unit 210 acquires the measured data of the sensor unit 10 (step S11). The measured data includes an angular velocity around the major axis of the shaft portion 3*a* and the head speed (the speed of the hitting portion 3*b*) from a backswing to follow-through. The control unit 21 may perform processes subsequent to step S12 in real time when first measured data in the swing motion (also including a standstill motion) of the user 2 is acquired, or may perform the processes subsequent to step S12 after some or all of the series of measured data in the swing motion of the user 2 are acquired from the sensor unit 10.

Next, the exercise analysis unit 211 detects a timing of an impact of the golf club 3 (step S12).

Next, referring to the storage unit 24, the calculation unit 212 determines whether the type of golf club 3 of the user 2 is the neomallet type, the mallet type, or the pin type (step S13). In a case in which the calculation unit 212 determines that the type of golf club 3 of the user 2 is the neomallet type ("neomallet type" of S13), the process proceeds to step S14. In a case in which the calculation unit 212 determines that the type of golf club 3 of the user 2 is the mallet type ("mallet type" of S13), the process proceeds to step S15. In a case in which the calculation unit 212 determines that the type of golf club 3 of the user 2 is the pin type ("pin type" of S13), the process proceeds to step S16.

In the case in which the calculation unit 212 determines in step S13 that the type of golf club 3 is the "neomallet type", the calculation unit 212 calculates a deviation amount of the hitting position from the sweet spot using Expression (3) stored in the storage unit 24 (step S14).

For example, the calculation unit 212 acquires an angular velocity around the major axis of the shaft portion 3*a* at the time of an impact based on the angular velocity around the major axis of the shaft portion 3*a* acquired in step S11 and a timing of the impact detected in step S12. The calculation unit 212 acquires a head speed at the time of the impact based on the head speed acquired in step S11 and the timing of the impact detected in step S12. Then, the calculation unit 212 calculates the deviation amount of the hitting position from the sweet spot by dividing the angular velocity at the time of the impact by the head speed at the time of the impact and substituting a value obtained through the division into the independent variable of Expression (3). When the calculation unit 212 calculates the deviation amount of the hitting position, the process proceeds to step S17.

In a case in which the calculation unit 212 determines in step S13 that the type of golf club 3 is the "mallet type", the calculation unit 212 calculates the deviation amount of the hitting position from the sweet spot using Expression (4) stored in the storage unit 24 (step S15).

For example, the calculation unit 212 acquires the angular velocity around the major axis of the shaft portion 3*a* at the time of the impact based on the angular velocity around the major axis of the shaft portion 3*a* acquired in step S11 and the timing of the impact detected in step S12. The calculation unit 212 acquires the head speed at the time of the impact based on the head speed acquired in step S11 and the timing of the impact detected in step S12. Then, the calculation unit 212 calculates the deviation amount of the hitting position from the sweet spot by dividing the angular velocity at the time of the impact by the head speed at the time of the impact and substituting a value obtained through the division into the independent variable of Expression (4). When the calculation unit 212 calculates the deviation amount of the hitting position, the process proceeds to step S17.

In a case in which the calculation unit 212 determines in step S13 that the type of golf club 3 is the "pin type", the calculation unit 212 calculates the deviation amount of the hitting position from the sweet spot using Expression (2) stored in the storage unit 24 (step S16).

For example, the calculation unit 212 acquires the angular velocity around the major axis of the shaft portion 3*a* at the time of the impact based on the angular velocity around the major axis of the shaft portion 3*a* acquired in step S11 and the timing of the impact detected in step S12. The calculation unit 212 acquires the head speed at the time of the impact based on the head speed acquired in step S11 and the timing of the impact detected in step S12. Then, the calculation unit 212 calculates the deviation amount of the hitting position from the sweet spot by dividing the angular velocity at the time of the impact by the head speed at the time of the impact and substituting the value obtained through the division into the independent variable of Expression (4). When the calculation unit 212 calculates the deviation amount of the hitting position, the process proceeds to step S17.

The image generation unit 213 generates the image data including the information regarding the deviation amount calculated in step S14, S15, or S16 (step S17). Thus, the image data generated by the image generation unit 213 is displayed on the display unit 25 by the output processing unit 214, and the user 2 can ascertain the deviation amount of the hitting position according to the golf club 3 to be used.

In this way, the relation information is acquired in advance according to the type of golf club 3 and is stored in the storage unit 24. Then, the calculation unit 212 calculates the deviation amount of the hitting position using the relation information according to the type of golf club 3 used by the user 2.

Thus, the calculation unit 212 can calculate a more accurate deviation amount of the hitting position according to the type of golf club 3.

As described above, the relation information regarding the three types, the neomallet type, the mallet type, and the pin type, is stored in advance in the storage unit 24, and the calculation unit 212 calculates the deviation amount of the hitting position according to the type, but the invention is not limited thereto. For example, relation information regarding 2 types or relation information regarding 4 types or more may be stored in advance in the storage unit 24 and a deviation amount of the hitting position according to each type may be calculated.

The storage unit 24 may store the relation information regarding the golf club 3 according to a maker or a model number of the golf club 3. Then, the calculation unit 212 may receive the maker or the model number of the golf club 3 to be used from the user 2 and calculate a deviation amount of the hitting position according to the golf club 3.

As described above, the angular velocity around the major axis of the shaft portion 3a is divided by the speed of the hitting portion 3b, but may not be divided by the speed of the hitting portion 3b. That is, the correlation between the angular velocity around the major axis of the shaft portion 3a and the deviation amount of the hitting position may be calculated for each type of golf club 3 and the deviation amount of the hitting position may be calculated.

Fourth Embodiment

Next, a fourth embodiment will be described with reference to the drawings. In the third embodiment, the relation information according to the type of golf club 3 is stored in the storage unit 24. In the fourth embodiment, however, relation information which can correspond to various types is stored in the storage unit 24. Hereinafter, differences from each of the foregoing embodiments will be described.

Figure 18:
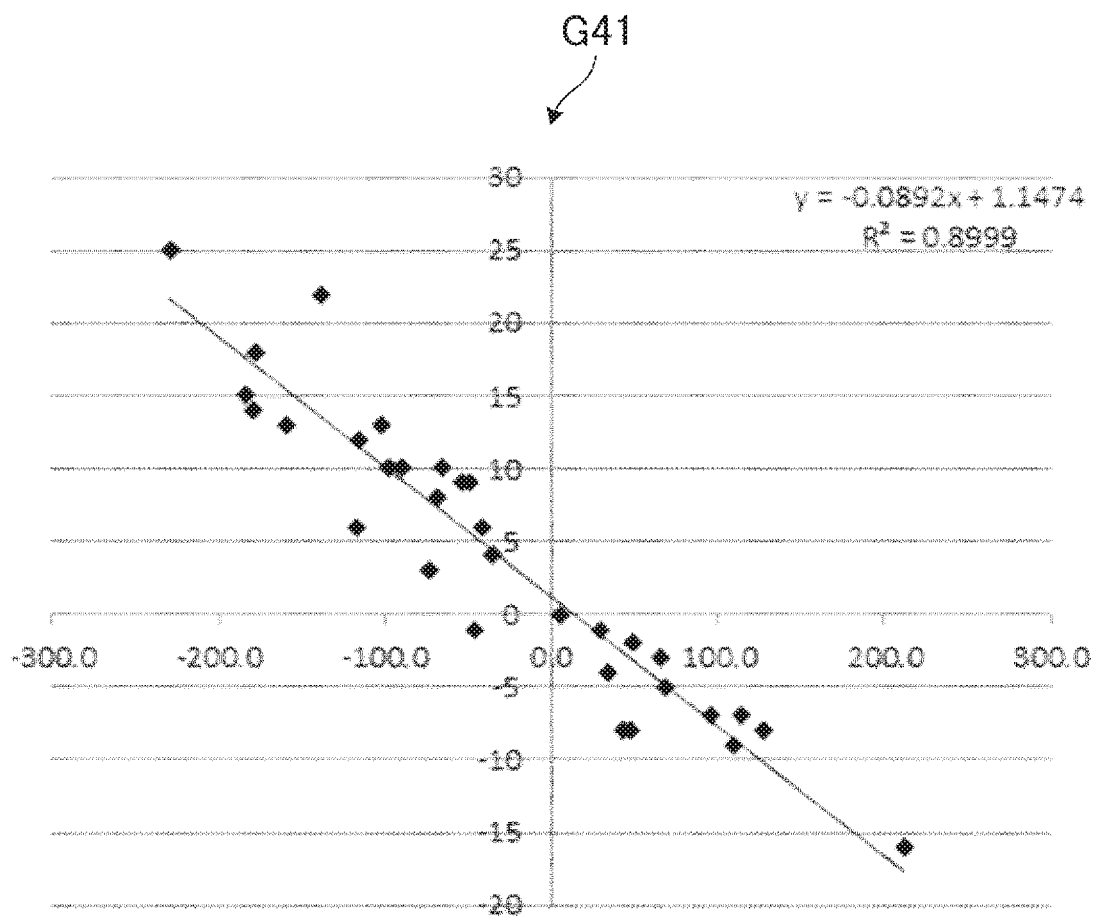
FIG. 18 is a graph diagram illustrating an example of relation information according to fourth embodiment.

FIG. 18 is a graph diagram illustrating an example of relation information according to fourth embodiment. The horizontal axis of a graph G41 illustrated in FIG. 18 represents a value obtained by dividing an angular velocity by a head speed. The vertical axis of the graph G41 represents a deviation amount of a hitting position.

Black rhombuses in the graph G41 plot GyroY/HS 51c and the hitting point measurement value 51d in FIG. 11, GyroY/HS 61c and the hitting point measurement value 61d in FIG. 13, and GyroY/HS 71c and the hitting point measurement value 71d in FIG. 15 on the graph G41. That is, the black rhombuses in the graph G41 plot GyroY/HS and the hitting point measurement values of the pin type, the neomallet type, and the mallet type on the graph G41.

As indicated in the graph G41, it is recognized that GyroY/HS and the hitting point measurement values of the pin type, the neomallet type, and the mallet type have correlation, and the correlation is indicated in a linear expression. A coefficient and an interception of the linear expression can be obtained by regression analysis. In the case of the example of FIG. 18, the linear expression is indicated in Expression (5) below.

$$y=-0.0892x+1.1474 \qquad (5)$$

A contribution ratio is "$R^2=0.8999$".

Expression (5) is stored in advance in the storage unit 24, as in each of the foregoing embodiments. Thus, referring to the storage unit 24, the calculation unit 212 can calculate the deviation amount of the hitting position even when the user 2 uses any one type of the golf club 3 of the pin type, the neomallet type, and the mallet type. [0164]

In this way, the relation information indicates relations between angular velocities and the deviation amounts in various types of golf club 3. Thus, the calculation unit 212 can calculate the appropriate deviation amounts of the hitting positions even when the user 2 uses various types of golf clubs 3.

Fifth Embodiment

Next, a fifth embodiment will be described with reference to the drawings. In the fifth embodiment, a hitting point measurement value in the horizontal direction measured by an acquirer is corrected with a hitting point measurement value in the vertical direction and a lie angle of the golf club 3.

Figure 19:
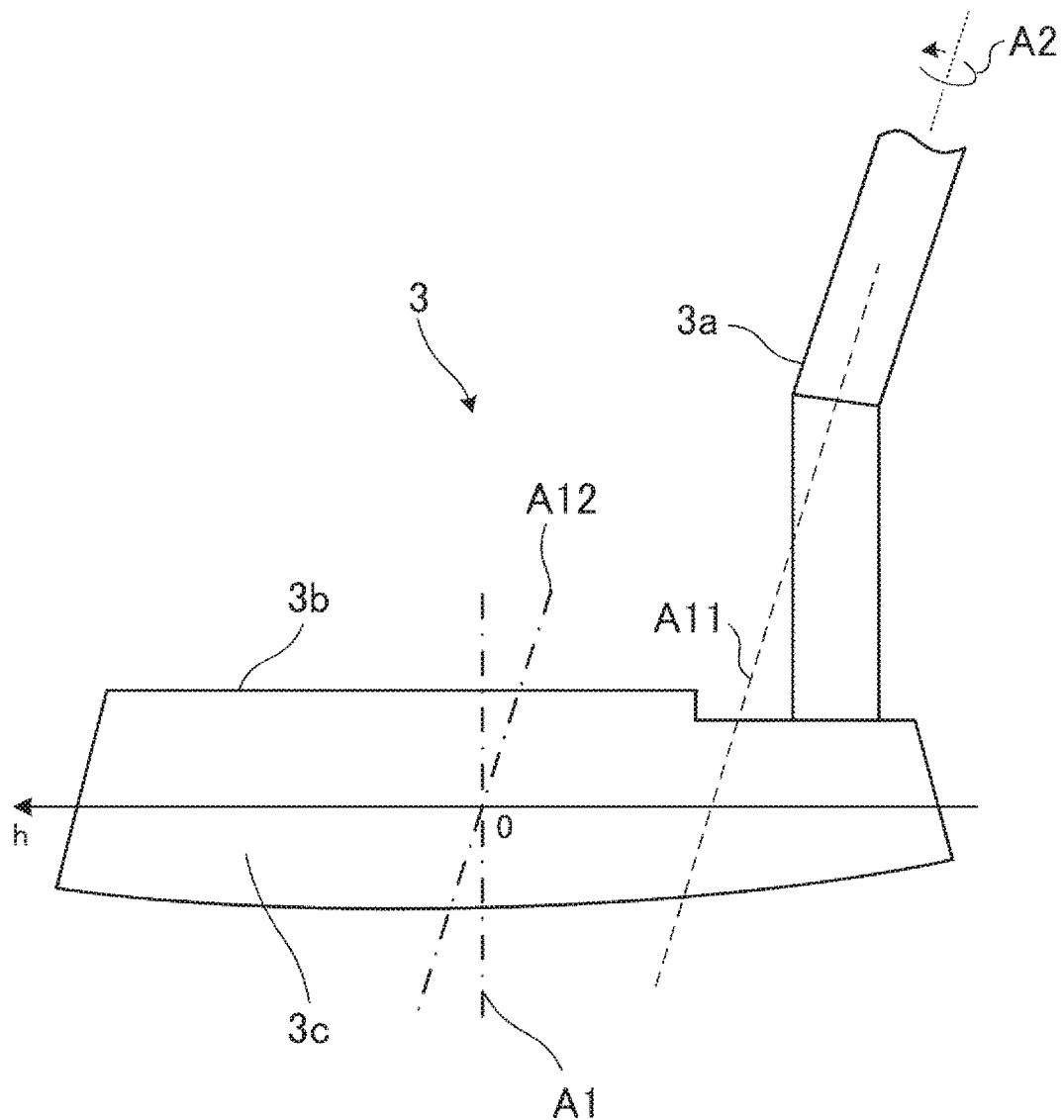
FIG. 19 is a diagram for describing correction of a hitting point measurement value in a horizontal direction according to a fifth embodiment.

FIG. 19 is a diagram for describing correction of a hitting point measurement value in a horizontal direction according to the fifth embodiment. In FIG. 19, the same reference numerals as those of FIG. 2 are given and the description thereof will be omitted. In FIG. 19, a major axis A11 of the shaft portion 3a is illustrated.

The standard line set on the hitting surface 3c may not be set vertically, as indicated by a one-dot chain line A1. For example, as illustrated in a one-dot chain line A12, the standard line may be set to be parallel to a major axis A11. That is, the standard line set on the hitting surface 3c may be set to have the same angle as a lie angle.

As indicated by the one-dot chain line A12, in a case in which the standard line is set to have the same angle as the lie angle, a distance of the hitting position from the standard line in the horizontal direction is changed in accordance with the lie angle of the golf club 3 and the height of a hitting position of a ball. For example, even when the height of the hitting position is different despite the fact that the hitting position is the same in the horizontal direction, a distance of the hitting position from the standard line (the one-dot chain line A12) is different. Accordingly, in the fifth embodiment, a hitting point measurement value in the horizontal direction is corrected in accordance with the hitting point measurement value in the vertical direction, and the lie angle of the golf club 3.

An expression for correcting the hitting point measurement value in the horizontal direction of the hitting surface 3c is expressed as in Expression (6) below.

$$Hm=H+V/\tan\theta \qquad (6)$$

"Hm" is a hitting point measurement value in the horizontal direction after correction. "H" is a hitting point measurement value in the horizontal direction before correction. That is, "H" is a hitting point measurement value in the horizontal direction acquired using a marker or the like by an acquirer and is a distance from the origin (for example, "0" of the h axis in FIG. 19) decided by the acquirer. is a hitting point measurement value in the vertical direction and is a height from the sole of the hitting portion 3b. A hitting point measurement value "V" in the vertical direction is similarly acquired in accordance with a marker or the like by the acquirer as in the hitting point measurement value "H" in the horizontal direction. "θ" is a lie angle (rad) of the golf club 3.

From Expression (6), a hitting point measurement value in the horizontal direction is corrected to be larger as the hitting point measurement value in the vertical direction is larger (that is, "Hm" is larger as "V" of the second term of the right side of Expression (6) is larger). As the lie angle "θ" of the golf club 3 is larger (as the major axis of the shaft portion 3a is closer to the vertical side), an influence of correction of the hitting point measurement value in the vertical direction or the hitting point measurement value in the horizontal direction is smaller (that is, the second term of the right side of Expression (6) is smaller).

Figures 20, 21:
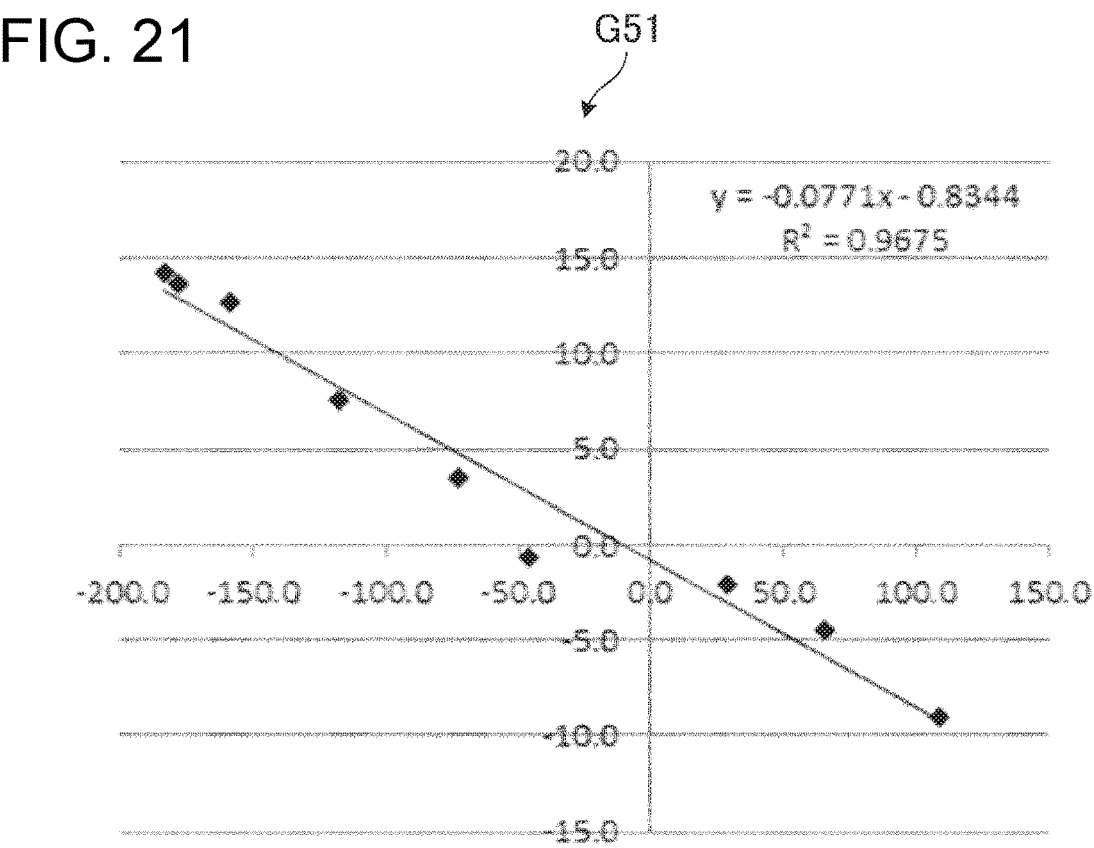
FIG. 20 is a diagram illustrating an example of relation information.
FIG. 21 is a graph diagram illustrating an example of the relation information of FIG. 20.

FIG. 20 is a diagram illustrating an example of relation information. As illustrated in FIG. 20, relation information 81 includes GyroY 81a, HS 81b, GyroY/HS 81c, a horizontal hitting point measurement value 81d, a height hitting point measurement value 81e, and a height correction horizontal hitting point position 81f. GyroY 81a, HS 81b, GyroY/HS 81c, and the horizontal hitting point measurement value 81d are the same as GyroY 51a, HS 51b, GyroY/HS 51c, and the hitting point measurement value 51d described in FIG. 11, and thus the description thereof will be omitted. [0174]

The height hitting point measurement value 81e is a hitting position in the vertical direction of the hitting surface 3c. The height hitting point measurement value 81e indicates a height from the sole of the hitting portion 3b. The height hitting point measurement value 81e is acquired in advance using a marker or the like by the acquirer as in the horizontal hitting point measurement value 81d.

The height correction horizontal hitting point position 81f is a value obtained by correcting the horizontal hitting point measurement value 81d with Expression (6) above. In the relation information 81 of FIG. 20, the height correction horizontal hitting point position 81f is calculated using "70 degrees" (1.22 rad) as a lie angle of the golf club 3.

FIG. 21 is a graph diagram illustrating an example of the relation information of FIG. 20. The horizontal axis of a graph G51 illustrated in FIG. 21 represents a value obtained by dividing an angular velocity by a head speed. The vertical axis of the graph G51 represents a deviation amount of a hitting position. Black rhombuses in the graph G51 plot GyroY/HS 81c and the height correction horizontal hitting point position 81f of the relation information 81 in FIG. 20 on the graph G51.

As indicated in the graph G51, it is recognized that GyroY/HS 81c and the height correction horizontal hitting point position 81f have correlation, and the correlation is indicated in a linear expression. A coefficient and an interception of the linear expression can be obtained by regression analysis. In the case of the example of FIG. 21, the linear expression is indicated in Expression (7) below.

$$y=-0.0771x-0.8344 \tag{7}$$

A contribution ratio is "$R^2=0.9675$".

Expression (7) is stored in advance in the storage unit 24, as in each of the foregoing embodiments. Thus, referring to the storage unit 24, the calculation unit 212 can calculate the deviation amount of the hitting position from the sweet spot.

In this way, the hitting point measurement value of the relation information in the horizontal direction is corrected in accordance with the hitting point measurement value and the lie angle of the shaft portion 3a in the vertical direction. Thus, the calculation unit 212 can calculate an appropriate deviation amount of the hitting position.

The storage unit 24 may store the relation information corrected at various lie angles. Then, the calculation unit 212 may calculate the deviation amount with reference to the relation information according to the lie angle of the golf club 3 used by the user 2. Thus, the calculation unit 212 can calculate a more appropriate deviation amount of the hitting position.

To improve the contribution ratio, the hitting point measurement value in the horizontal direction may be corrected by adding a predetermined angle to a lie angle.

Figures 22, 23:
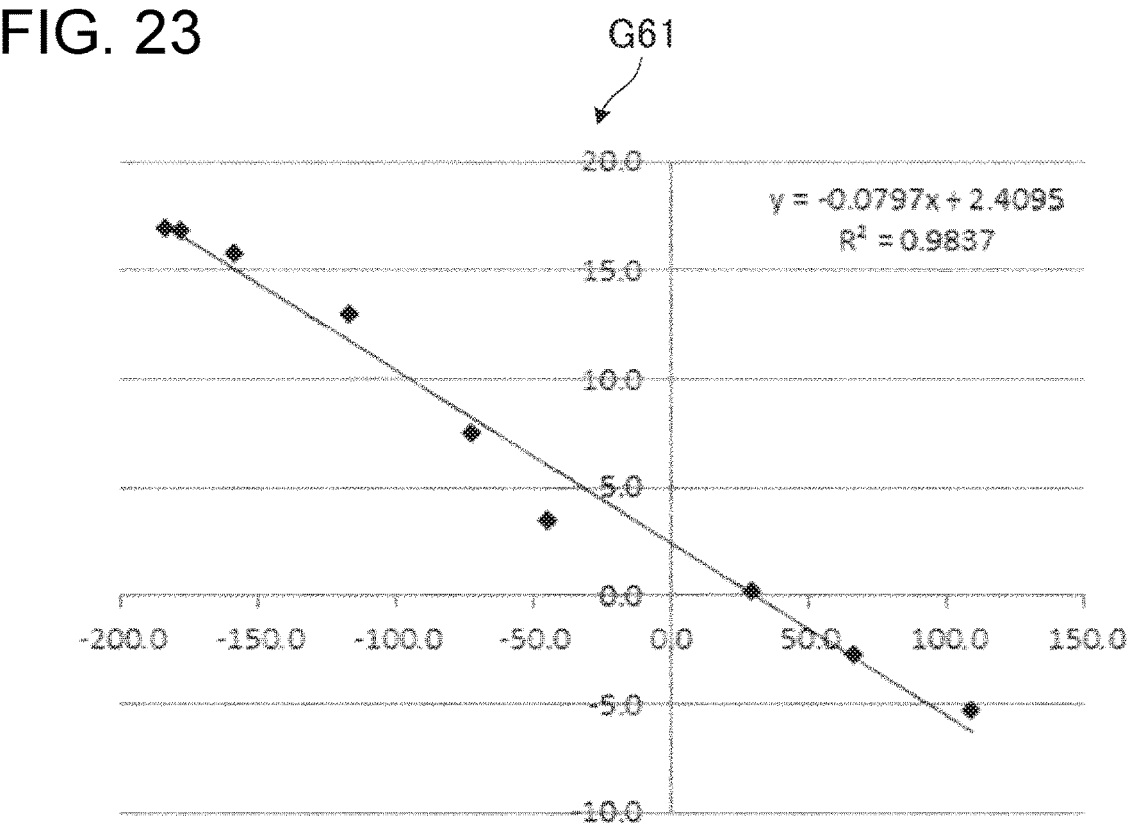
FIG. 22 is a diagram illustrating an example of relation information in a case in which a predetermined angle is added to a lie angle.
FIG. 23 is a graph diagram illustrating an example of the relation information of FIG. 22.

FIG. 22 is a diagram illustrating an example of relation information in a case in which the predetermined angle is added to a lie angle. In FIG. 22, the same reference numerals are given to the same elements as those of FIG. 20. As illustrated in FIG. 22, the relation information 91 is different from the relation information 81 of FIG. 20 in a height correction horizontal hitting point position 91a.

The height correction horizontal hitting point position 91a is a value obtained by correcting the horizontal hitting point measurement value 81d in Expression (6) above. In the relation information 91 of FIG. 22, the height correction horizontal hitting point position 91a is calculated by adding "−20 degrees" to a lie angle "70 degrees" of the golf club 3. That is, the height correction horizontal hitting point position 91a is calculated using "50 degrees" (0.87 rad) as "θ" of Expression (6).

FIG. 23 is a graph diagram illustrating an example of the relation information of FIG. 22. The horizontal axis of a graph G61 illustrated in FIG. 23 represents a value obtained by dividing an angular velocity by a head speed. The vertical axis of the graph G61 represents a deviation amount of a hitting position. Black rhombuses in the graph G61 plot GyroY/HS 81c and the height correction horizontal hitting point position 91a of the relation information 91 in FIG. 22 on the graph G61.

As indicated in the graph G61, it is recognized that GyroY/HS 81c and the height correction horizontal hitting point position 91a have correlation, and the correlation is indicated in a linear expression. A coefficient and an interception of the linear expression can be obtained by regression analysis. In the case of the example of FIG. 23, the linear expression is indicated in Expression (8) below.

$$y=-0.0797x+2.4095 \tag{8}$$

A contribution ratio is "$R^2=0.9837$".

The contribution ratio "$R^2=0.9837$" of Expression (8) is greater than the contribution ratio "$R^2=0.9675$" of Expression (7). That is, by adding a predetermined angle "−50 degrees" to a lie angle "70 degrees" of the golf club 3, the correlation between GyroY/HS and the height correction horizontal hitting point position becomes stronger.

In this way, to improve the contribution ratio, the hitting point measurement value in the horizontal direction may be corrected by adding a predetermined angle to the lie angle. Thus, the calculation unit 212 can calculate an appropriate deviation amount of the hitting position.

Sixth Embodiment

Next, a sixth embodiment will be described with reference to the drawings. In the second embodiment, the relation between a value obtained by dividing an angular velocity of the shaft portion 3a by a speed of the hitting portion 3b and a deviation amount of the hitting position is set as the relation information. In the sixth embodiment, a relation between a value obtained by dividing an angular velocity of the shaft portion 3a by a takeback distance and a deviation amount of a hitting position is assumed to be relation information.

Figure 24:
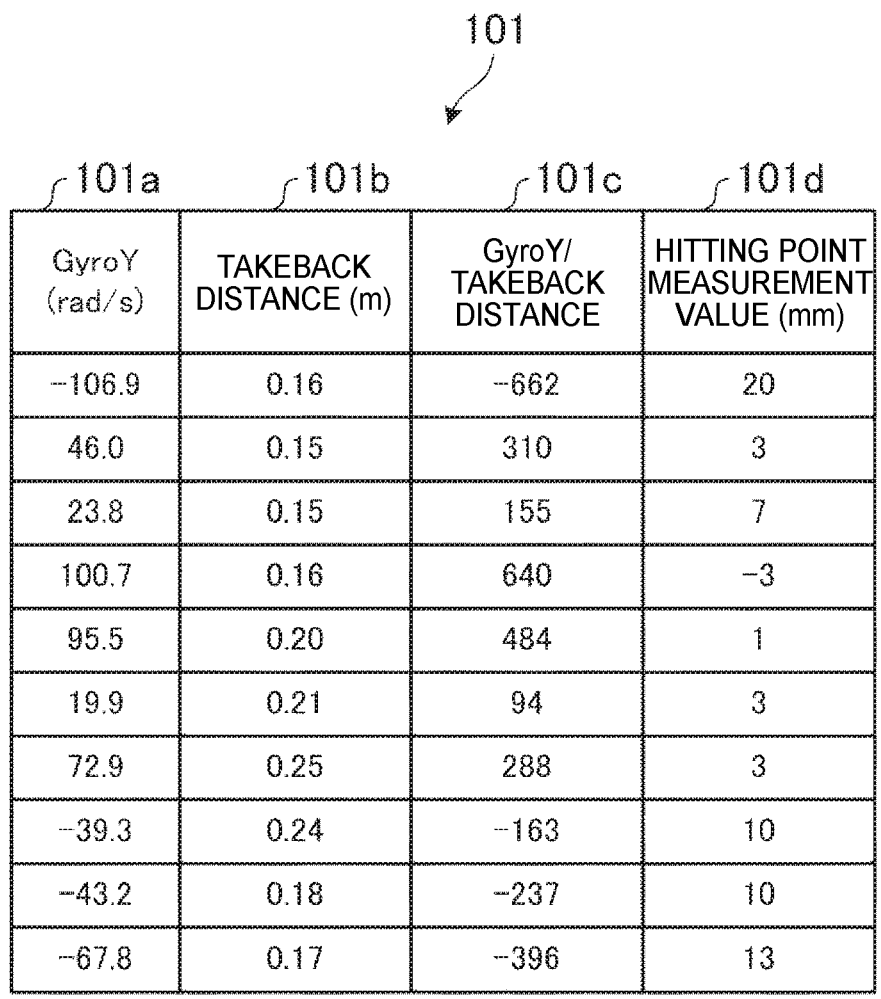
FIG. 24 is a diagram illustrating an example of relation information according to a sixth embodiment.

FIG. 24 is a diagram illustrating an example of relation information according to the sixth embodiment. As illustrated in FIG. 24, relation information 101 includes GyroY 101a, a takeback distance 101b, GyroY/takeback distance 101c, and a hitting point measurement value 101d. GyroY 101a and the hitting point measurement value 101d are the same as GyroY 51a and the hitting point measurement value 51d described in FIG. 11, and thus the description thereof will be omitted.

The takeback distance 101b is a distance between an address to a top of the hitting portion 3b. For example, the takeback distance 101b is acquired in advance by an acquirer using the exercise analysis device 20. The exercise analysis unit 211 can calculate the takeback distance using an exercise analysis model and information regarding the position and attitude of the sensor unit 10.

GyroY/takeback distance 101c is a value obtained by dividing GyroY 101a by the takeback distance 101b.

Figure 25:
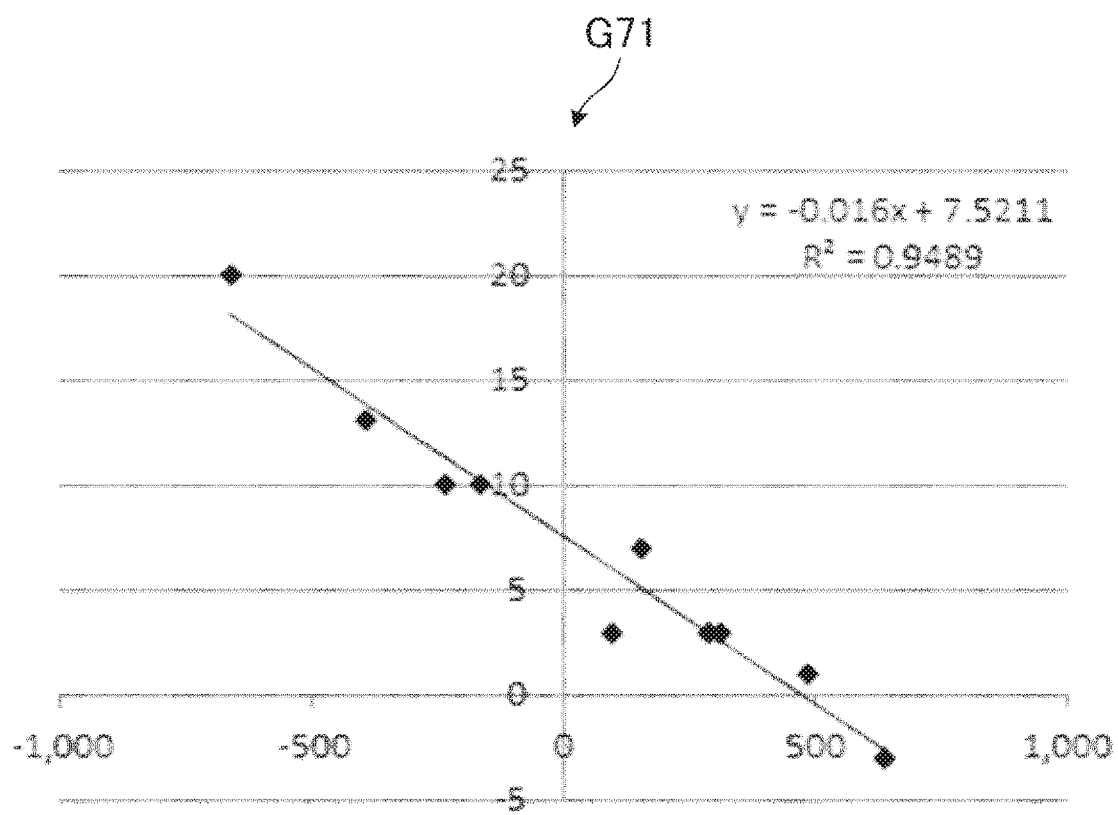
FIG. 25 is a graph diagram illustrating an example of the relation information of FIG. 24.

FIG. 25 is a graph diagram illustrating an example of the relation information of FIG. 24. The horizontal axis of a graph G71 illustrated in FIG. 25 represents a value obtained by dividing an angular velocity by a takeback distance. The vertical axis of the graph G71 represents a deviation amount of a hitting position. Black rhombuses in the graph G71 plot GyroY/takeback distance 101c and the hitting point measurement value 101d of the relation information 101 in FIG. 24 on the graph G71.

As indicated in the graph G71, it is recognized that GyroY/takeback distance 101c and the hitting point measurement value 101d have correlation, and the correlation is indicated in a linear expression. A coefficient and an interception of the linear expression can be obtained by regression analysis. In the case of the example of FIG. 25, the linear expression is indicated in Expression (9) below.

$$y=-0.016x+7.5211 \quad (9)$$

A contribution ratio is "$R^2=0.9489$".

Expression (9) is stored in advance in the storage unit 24, as in each of the foregoing embodiment. Thus, referring to the storage unit 24, the calculation unit 212 can calculate the deviation amount of the hitting position from the sweet spot.

The takeback distance and a speed of the hitting portion 3b at the time of an impact are considered to have a proportional relation. For example, it is considered that a speed of the hitting portion 3b at the time of an impact is larger as the takeback distance is larger. Accordingly, it is considered that the relation information according to the sixth embodiment has stronger correlation than the relation information of the first embodiment, as in the second embodiment.

In this way, the relation information indicates a relation between the deviation amount of the hitting position and the value obtained by dividing the angular velocity around the major axis of the shaft portion 3a by the takeback distance of the hitting portion 3b. Then, the calculation unit 212 divides the angular velocity around the major axis of the shaft portion 3a at the time of the impact by the takeback distance of the hitting portion 3b and calculates the deviation amount of the hitting position with reference to the relation information based on the value obtained through the division.

Thus, the exercise analysis device 20 can calculate a more accurate deviation amount of the hitting position.

Seventh Embodiment

Next, a seventh embodiment will be described with reference to the drawings. In the sixth embodiment, the relation between a value obtained by dividing an angular velocity of the shaft portion 3a by the takeback distance of the hitting portion 3b and a deviation amount of the hitting position is set as the relation information. In the seventh embodiment, a relation between a value obtained by dividing an angular velocity of the shaft portion 3a by a takeback angle and a deviation amount in a hitting position is assumed to be relation information.

Figure 26:
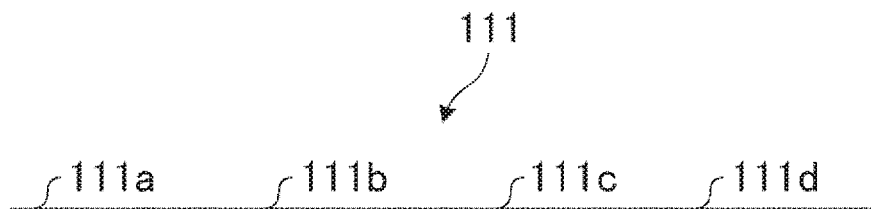
FIG. 26 is a diagram illustrating an example of relation information according to a seventh embodiment.

FIG. 26 is a diagram illustrating an example of relation information according to a seventh embodiment. As illustrated in FIG. 26, relation information 111 includes GyroY 111a, a takeback angle 111b, GyroY/takeback angle 111c, and a hitting point measurement value 111d. GyroY 111a and the hitting point measurement value 111d are the same as GyroY 51a and the hitting point measurement value 51d described in FIG. 11, and thus the description thereof will be omitted.

The takeback angle 111b is an angle between the hitting portion 3b at the time of an address and the hitting portion 3b at the time of a top. For example, the takeback angle 111b is acquired in advance by an acquirer using the exercise analysis device 20. The exercise analysis unit 211 can calculate the takeback angle using a exercise analysis model and information regarding the position and attitude of the sensor unit 10.

GyroY/takeback angle 111c is a value obtained by dividing GyroY 111a by the takeback angle 111b.

Figure 27:
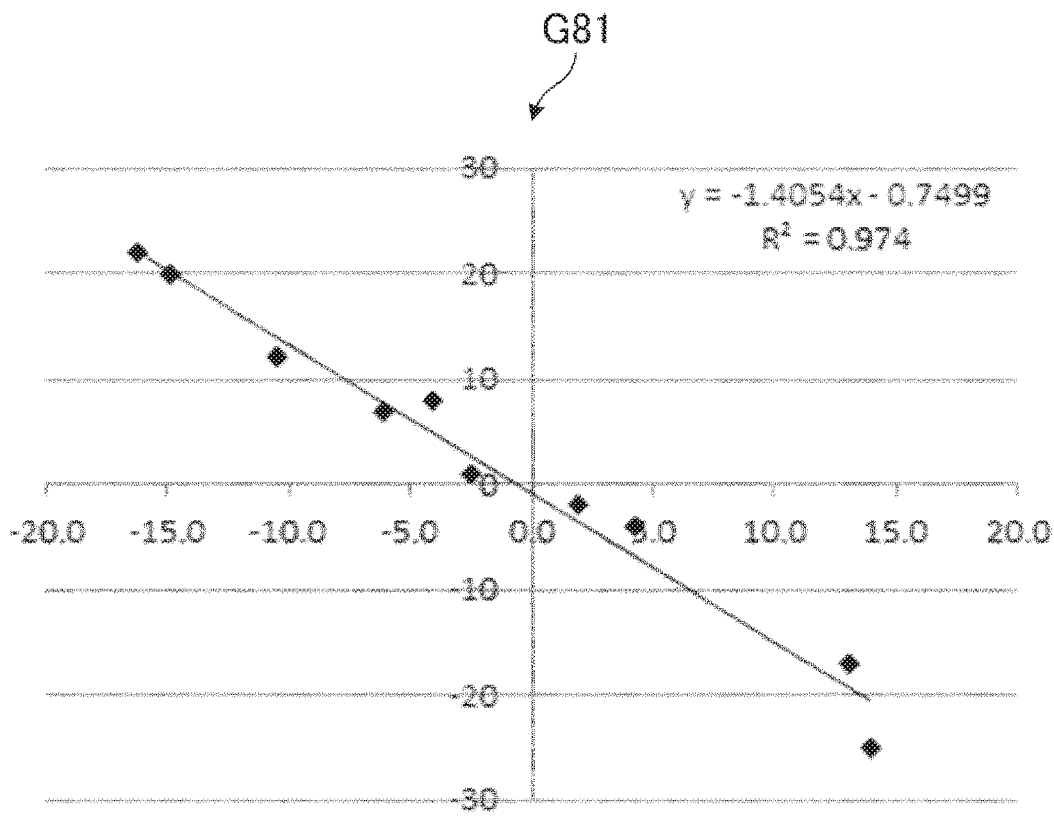
FIG. 27 is a graph diagram illustrating an example of the relation information of FIG. 26.

FIG. 27 is a graph diagram illustrating an example of the relation information of FIG. 26. The horizontal axis of a graph G81 illustrated in FIG. 27 represents a value obtained by dividing an angular velocity by a takeback angle. The vertical axis of the graph G81 represents a deviation amount of a hitting position. Black rhombuses in the graph G81 plot GyroY/takeback angle 111c and the hitting point measurement value 111d of the relation information 111 in FIG. 26 on the graph G81.

As indicated in the graph G81, it is recognized that GyroY/takeback angle 111c and the hitting point measurement value 111d have correlation, and the correlation is indicated in a linear expression. A coefficient and an interception of the linear expression can be obtained by regression analysis. In the case of the example of FIG. 27, the linear expression is indicated in Expression (10) below.

$$y=-1.454x-0.7499 \quad (10)$$

A contribution ratio is "$R^2=0.974$".

Expression (10) is stored in advance in the storage unit 24, as in each of the foregoing embodiment. Thus, referring to the storage unit 24, the calculation unit 212 can calculate the deviation amount of the hitting position from the sweet spot.

The takeback angle and a speed of the hitting portion 3b at the time of an impact are considered to have a proportional relation. For example, it is considered that a speed of the hitting portion 3b at the time of an impact is larger as the takeback angle is larger. Accordingly, it is considered that the relation information according to the seventh embodiment has stronger correlation than the relation information of the first embodiment, as in the second embodiment.

In this way, the relation information indicates a relation between the deviation amount of the hitting position and the value obtained by dividing the angular velocity around the major axis of the shaft portion 3a by the takeback angle of the hitting portion 3b. Then, the calculation unit 212 divides the angular velocity around the major axis of the shaft portion 3a at the time of the impact by the takeback angle of the hitting portion 3b and calculates the deviation amount of the hitting position with reference to the relation information based on the value obtained through the division.

Thus, the exercise analysis device 20 can calculate a more accurate deviation amount of the hitting position.

Eigth Embodiment

Next, an eighth embodiment will be described with reference to the drawings. In the eighth embodiment, an average value of angular velocities before an impact is calculated and the calculated average value of the angular velocities is subtracted from an angular velocity at the time of the impact to set an angular velocity at the time of the impact.

Figure 28:
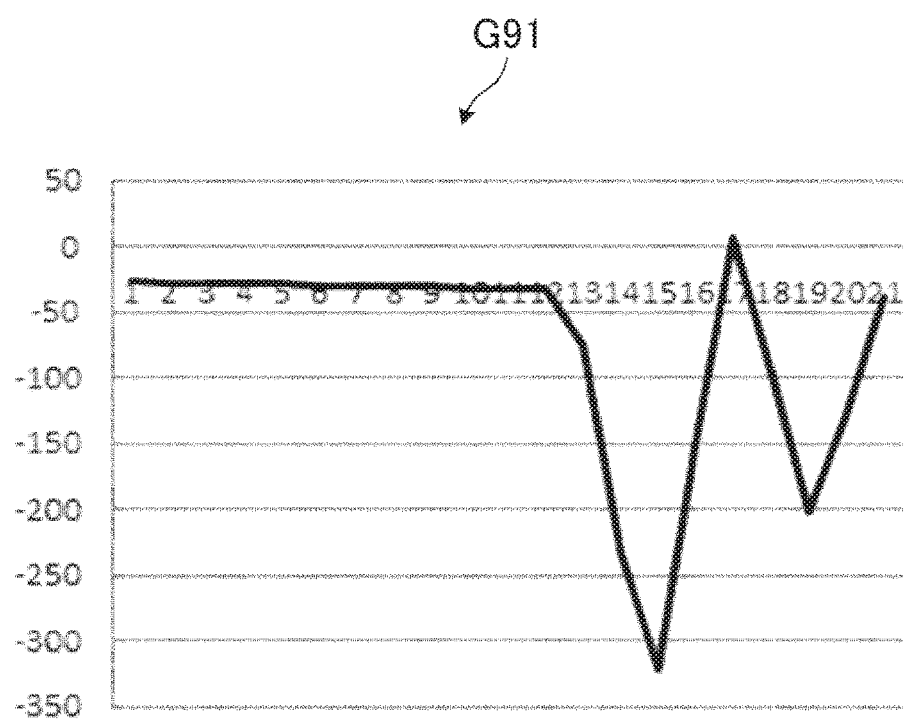
FIG. 28 is a diagram for describing angular velocity calculation according to an eighth embodiment.

FIG. 28 is a diagram for describing angular velocity calculation according to the eighth embodiment. The horizontal axis of a graph G91 illustrated in FIG. 28 represents a sample point of an angular velocity. The vertical axis of the graph G91 represents an angular velocity. A waveform shown in the graph G91 indicates an angular velocity around the major axis of the shaft portion 3a acquired by the sensor information acquisition unit 210.

In the waveform shown in the graph G91, a time at which the absolute value is the largest is the time of the impact. For example, in the example of the graph G91, a sample point "15" is the time of the impact.

The calculation unit 212 calculates an average value of a predetermined number of angular velocities before an impact. Then, the calculation unit 212 subtracts the calculated average value of the angular velocities from the angular velocity at the time of the impact. The predetermined number before the impact is, for example, "10". A point before an impact may be set using a sample point immediately before the time of the impact as a starting point or may be set using a sample point located a predetermined number back from the time of the impact as a starting point.

For example, in a case in which the point before the impact is set using a sample point immediately before the time of the impact as the starting point, the calculation unit 212 calculates an average value of angular velocities of 10 samples, sample point s"5, 6, . . . , 13, and 14". Then, the calculation unit 212 subtracts the calculated average value of the angular velocities of the 10 samples from an angular velocity of sample point "15" at the time of the impact and sets a value obtained through the subtraction as an angular velocity at the time of the impact. Alternatively, for example, in a case in which the point before the impact is set using a sample point three immediately before the time of the impact as a starting point, the calculation unit 212 calculates an average value of the angular velocities of 10 samples, sample points "3, 4, . . . , 11, and 12". Then, the calculation unit 212 may subtract the calculated average value of the angular velocities of 10 samples from an angular velocity of the sample point "15" at the time of the impact and set a value obtained through the subtraction as an angular velocity at the time of the impact.

The foregoing calculation of the calculation unit 212 subtracts an offset of the sensor unit 10 from the angular velocity at the time of the impact. That is, through the foregoing calculation, the calculation unit 212 is configured to calculate an angular velocity generated around the major axis of the shaft portion 3a due to hitting of a ball.

In this way, the calculation unit 212 calculates the average value of the predetermined number of angular velocities before the impact, subtracts the calculated average value of the angular velocities from the angular velocity at the time of the impact, and calculates a deviation amount of a hitting position using the subtracted value.

Thus, the exercise analysis device 20 can calculate a more accurate deviation amount of the hitting position.

In each of the foregoing embodiments, a putter has been described as an example of the golf club 3, but the invention is not limited thereto. For example, the invention can also be applied to a club such as a driver or an iron.

In each of the foregoing embodiments, the exercise analysis system (exercise analysis device) that analyzes a golf swing has been exemplified, but the invention can be applied to an exercise analysis system (exercise analysis device) that analyzes various exercise swings of in tennis or a baseball game.

The foregoing embodiments can be combined. For example, the third embodiment may be combined with any one of, for example, the fifth, sixth, and seventh embodiments.

The functional configurations of the above-described exercise analysis system are classified according to the main processing content to easily understand the configuration of the exercise analysis system. The invention is not limited to the classification method or the names of the constituent elements. The configuration of the exercise analysis system can also be classified into more constituent elements according to the processing content. The configuration of the exercise analysis system can also be classified so that one constituent element performs more processes. The process of each constituent element may be realized single hardware or a plurality of pieces of hardware.

The processing units of the above-described flowcharts are classified according to the main processing content to easily understand the processes of the exercise analysis system. The invention is not limited to the processing unit partition method or the names of the constituent elements. The processes of the exercise analysis system can also be classified into more processing units according to the processing content. The processes of the exercise analysis system can also be classified so that one processing unit includes more processes. The procedure of the processes is not limited to the flowchart either.

The embodiments of the invention have been described above, but the technical scope of the invention is not limited to the scope described in the foregoing embodiments. It should be apparent to those skilled in the art that various modifications and improvements can be added to the foregoing embodiments. It is apparent from the description of the claims that forms to which the modifications or the improvements are added can be included in the technical scope of the invention. The invention can be provided as an exercise analysis method, a program of the exercise analysis device, and a recoding medium storing the program. In the foregoing embodiments, the sensor unit 10 and the exercise analysis device 20 have been described as separate elements, but the functions of the exercise analysis device 20 may be mounted on the sensor unit 10.

REFERENCE SIGNS LIST 1 exercise analysis system
2 user
3 golf club
3a shaft portion
3b hitting portion
3c hitting surface
10 sensor unit
20 exercise analysis device
21 control unit
210 sensor information acquisition unit
211 exercise analysis unit
212 calculation unit
213 image generation unit
214 output processing unit
22 communication unit
23 manipulation unit
24 storage unit
25 display unit
26 audio output unit
31 relation information
40 screen

The invention claimed is:

1. An exercise analysis device comprising:
a memory that stores relation information indicating a relationship of (i) an angular velocity generated around an axis in a longitudinal direction of a shaft portion of an exercise instrument and (ii) a distance between a sweet spot on a hitting surface of a hitting portion of the exercise instrument and an impact position; and
a controller that:
 acquires, from an angular velocity sensor, an angular velocity generated around the axis in the longitudinal direction of the shaft portion, and stores the angular velocity in the memory;
 detects, from the angular velocity, a timing of an impact and stores the timing in the memory;
 calculates the impact position using the angular velocity at the timing of the impact; and
 calculates the distance between the sweet spot and the impact position using the relation information.

2. The exercise analysis device according to claim 1, wherein the relation information is acquired based on a plurality of swing-and-impact events.

3. The exercise analysis device according to claim 1, wherein the relation information is acquired according to a shape of the hitting portion.

4. The exercise analysis device according to claim 1, wherein the controller (i) calculates an average value of a plurality of angular velocities generated around the axis in the longitudinal direction of the shaft portion before the impact, and (ii) subtracts the average value from the angular velocity generated by the impact, resulting in a subtracted value, wherein the calculation of the distance by the controller is performed based on the subtracted value.

5. An exercise analysis method comprising the steps of:
storing relation information indicating a relationship of (i) an angular velocity generated around an axis in a longitudinal direction of a shaft portion of an exercise instrument and (ii) a distance between a sweet spot on a hitting surface of a hitting portion of the exercise instrument and an impact position;
acquiring, from an angular velocity sensor, an angular velocity generated around the axis in the longitudinal direction of the shaft portion;
detecting, from the angular velocity, a timing of an impact;
calculating the impact position using the angular velocity at the timing of the impact; and
calculating the distance between the sweet spot and the impact position using the relation information.

6. The exercise analysis method according to claim 5, wherein the relation information acquired based on a plurality of swing-and-impact events.

7. The exercise analysis method according to claim 5, wherein the relation information is acquired according to a shape of the hitting portion.

8. The exercise analysis method according to claim 7, further comprising:
calculating an average value of a plurality of angular velocities generated around the axis in the longitudinal direction of the shaft portion before the impact, and (ii) subtracting the average value from the angular velocity generated by the impact, wherein the calculating the distance is performed based on the subtracted value.

9. A program causing a computer to perform the steps of:
storing, in a memory, relation information indicating a relationship of (i) an angular velocity generated around an axis in a longitudinal direction of a shaft portion of an exercise instrument and (ii) a distance between a sweet spot on a hitting surface of a hitting portion of the exercise instrument and an impact position;
acquiring, from an angular velocity sensor, an angular velocity generated around the axis in the longitudinal direction of the shaft portion, and storing the angular velocity in the memory;
detecting, from the angular velocity, a timing of an impact, and storing the timing in the memory;
calculating the impact position using the angular velocity at the timing of the impact; and
calculating the distance between the sweet spot and the impact position using the relation information.

10. A non-transitory recording medium that records a program causing a computer to perform the steps of:
storing, in a memory, relation information indicating a relationship of (i) an angular velocity generated around an axis in a longitudinal direction of a shaft portion of an exercise instrument and (ii) a distance between a sweet spot on a hitting surface of a hitting portion of the exercise instrument and an impact position;
acquiring, from an angular velocity sensor, an angular velocity generated around the axis in the longitudinal direction of the shaft portion, and storing the angular velocity in the memory;
detecting, from the angular velocity, a timing of an impact, and storing the timing in the memory;
calculating the impact position using the angular velocity at the timing of the impact; and
calculating the distance between the sweet spot and the impact position using the relation information.

11. An exercise analysis system comprising:
an inertial sensor that measures an angular velocity generated around an axis in a longitudinal direction of a shaft portion of an exercise instrument; and
an exercise analysis device including a controller that:
 stores, in a memory, relation information indicating a relationship of (i) an angular velocity generated around an axis in a longitudinal direction of a shaft portion of an exercise instrument and (ii) a distance between a sweet spot on a hitting surface of a hitting portion of the exercise instrument and an impact position;

acquires, from the inertial sensor, the angular velocity generated around the axis in the longitudinal direction of the shaft portion of the exercise instrument, and stores the angular velocity in the memory;
detects, from the angular velocity, a timing of an impact, and stores the timing in the memory;
calculates the impact position using the angular velocity at the timing of the impact; and
calculates the distance between the sweet spot and the impact position using the relation information.

* * * * *